(12) United States Patent
Liu

(10) Patent No.: US 12,379,385 B2
(45) Date of Patent: *Aug. 5, 2025

(54) METHODS OF TREATING PATIENTS AFFLICTED WITH IRRITABLE BOWEL SYNDROME, INFLAMMATORY BOWEL DISEASE OR CHRONIC GASTROINTESTINAL FUNCTIONAL DISORDERS BASED ON ASSESSMENT OF INTESTINAL BARRIER FUNCTION

(71) Applicant: Maximus Diagnostic Technologies LLC, Decatur, GA (US)

(72) Inventor: Julia J. Liu, Decatur, GA (US)

(73) Assignee: Maximus Diagnostic Technologies LLC, Decatur, GA (US)

( * ) Notice: Subject to any disclaimer, the term of this patent is extended or adjusted under 35 U.S.C. 154(b) by 7 days.

This patent is subject to a terminal disclaimer.

(21) Appl. No.: 18/212,542

(22) Filed: Jun. 21, 2023

(65) Prior Publication Data

US 2023/0349923 A1 Nov. 2, 2023

Related U.S. Application Data

(63) Continuation of application No. 16/847,134, filed on Apr. 13, 2020, now Pat. No. 11,693,015, which is a continuation of application No. 16/073,212, filed as application No. PCT/US2017/016152 on Feb. 2, 2017, now Pat. No. 10,663,473.

(60) Provisional application No. 62/434,741, filed on Dec. 15, 2016, provisional application No. 62/290,201, filed on Feb. 2, 2016.

(51) Int. Cl.
| | |
|---|---|
| *G01N 33/68* | (2006.01) |
| *A61K 31/4035* | (2006.01) |
| *A61K 31/4245* | (2006.01) |
| *A61K 31/427* | (2006.01) |
| *A61K 31/496* | (2006.01) |
| *A61K 31/519* | (2006.01) |
| *A61K 39/00* | (2006.01) |
| *A61P 1/00* | (2006.01) |
| *C07K 16/24* | (2006.01) |
| *C07K 16/28* | (2006.01) |

(52) U.S. Cl.
CPC ..... *G01N 33/6893* (2013.01); *A61K 31/4035* (2013.01); *A61K 31/4245* (2013.01); *A61K 31/427* (2013.01); *A61K 31/496* (2013.01); *A61K 31/519* (2013.01); *A61P 1/00* (2018.01); *C07K 16/241* (2013.01); *C07K 16/2839* (2013.01); *A61K 2039/505* (2013.01); *A61K 2039/55* (2013.01); *C07K 2317/21* (2013.01); *C07K 2317/24* (2013.01); *G01N 2800/065* (2013.01); *G01N 2800/52* (2013.01)

(58) Field of Classification Search
CPC ............ G01N 33/6893; A61K 31/4035; A61K 31/4245; A61K 31/427; A61K 31/519; A61P 1/00; C07K 16/241; C07K 16/2839; C07K 16/505
See application file for complete search history.

(56) References Cited

U.S. PATENT DOCUMENTS

| | | | |
|---|---|---|---|
| 5,292,636 | A | 3/1994 | Kung et al. |
| 10,663,473 | B2 | 5/2020 | Liu |
| 2003/0040681 | A1 | 2/2003 | Ng et al. |
| 2005/0136492 | A1 | 6/2005 | Phelps et al. |
| 2006/0105419 | A1 | 5/2006 | Blankenberg et al. |
| 2007/0111934 | A1 | 5/2007 | Doi et al. |
| 2010/0003196 | A1 | 1/2010 | Gray |
| 2010/0222228 | A1 | 9/2010 | Thielemans et al. |
| 2012/0115746 | A1 | 5/2012 | Pasricha et al. |
| 2015/0202329 | A1 | 7/2015 | Liu et al. |
| 2019/0033326 | A1 | 1/2019 | Liu |
| 2020/0110089 | A1 | 4/2020 | Liu et al. |

FOREIGN PATENT DOCUMENTS

| | | |
|---|---|---|
| CN | 101184491 A | 5/2008 |
| CN | 105473732 A | 4/2016 |
| JP | 2015-502740 A | 1/2015 |
| WO | 2008043566 A2 | 4/2008 |
| WO | 2010/062663 A1 | 6/2010 |
| WO | 2011128429 A1 | 10/2011 |
| WO | 2012125530 A1 | 9/2012 |
| WO | 2013/080050 A2 | 6/2013 |

(Continued)

OTHER PUBLICATIONS

Motta, et al., "Nod-Like Receptors: Versatile Cytosolic Sentinels," Physiological Reviews, vol. 95, pp. 149-178, 2015.

(Continued)

*Primary Examiner* — Robert S Landsman
(74) *Attorney, Agent, or Firm* — Nutter McClennen & Fish LLP

(57) ABSTRACT

In some embodiments, the invention provides a method for identifying an agent beneficial to treat a patient with inflammatory bowel disease comprising: a) determining a status of an intestinal barrier in the patient; and b) categorizing the status as severe dysfunction or moderate dysfunction, wherein a patient categorized as having severe dysfunction is identified as a patient who will benefit from treatment with an agent selected from the group consisting of an anti-TNF agent and/or an anti-IL-12/23 agent, and a patient categorized as having moderate dysfunction is identified as a patient who will benefit from treatment with an anti-integrin agent, an anti-janus kinase agent, and/or and a sphingosine-1-phosphate receptor agonist agent.

15 Claims, 5 Drawing Sheets

(56) References Cited

FOREIGN PATENT DOCUMENTS

| | | |
|---|---|---|
| WO | 2014/039699 A1 | 3/2014 |
| WO | 2014/055824 A1 | 4/2014 |
| WO | 2015/083085 A1 | 6/2015 |
| WO | 2017136511 A1 | 8/2017 |

OTHER PUBLICATIONS

Neudecker, et al., "Myeloid-derived miR-223 regulates intestinal inflammation via repression of the NLRP3 inflammasome," Journal of Experimental Medicine, vol. 214, No. 6, pp. 1737-1752, 2017.
Neurath MF., "New targets for mucosal healing and therapy in inflammatory bowel diseases," Mucosal Immunology, vol. 7, No. 1, pp. 6-19, Oct. 2013.
Nishida, K., et al., "Interleukin-18 is a crucial determinant of vulnerability of the mouse rectum to psychosocial stress," The FASEB Journal 23(6): 1797-1805, 2009.
Notice of Hearing for Indian Patent Application No. 1991/DELNP/2015, dated Jan. 29, 2021, 3 pages.
Perez-Jeldres, et al., "Targeting Cytokine Signaling and Lymophcytle Traffic via Small Molecules in Inflammatory Bowel Disease: JAK Inhibitors and S1PR Agonists," Front Pharmacol, 2019, 10(212), pp. 1-15.
Prasuhn, et al. "Quantum Dot Peptide Biosensors for Monitoring Caspase 3 Proteolysis and Calcium Ions," ACS Nano, vol. 4, issue 9, 2010, pp. 5487-5497.
Puthia, et al. "Blastocystis ratti Induces Contact-Independent Apoptosis, F-Actin Rearrangement, and Barrier Function Disruption in IEC-6 Cells", Infection and Immunity, vol. 74, issue 7, 2006, pp. 4114-4123.
Rauch, et al., "NAIP-NLRC4 Inflammasomes Coordinate Intestinal Epithelial Cell Expulsion with Eicosanoid and IL-18 Release via Activation of Caspase-1 and -8," Immunity, vol. 46, pp. 649-659, Apr. 2017.
Richard, et al., "Cellular Uptake of Unconjugated TAT Peptide Involves Clathrin-dependent Endocytosis and Heparan Sulfate Receptors," The Journal of Biological Chemistry, vol. 280, No. 15, pp. 15300-15306, Apr. 2005.
Sandborn, W, "New Targets for Small Molecules in Inflammatory Bowel Disease," Gastroenterology & Hepatology, vol. 11, Issue 5, pp. 338-340 (May 2015).
Schreiber, et al., "Increased Activation of Isolated Intestinal Lamina Propria Mononuclear Cells in Inflammatory Bowel Disease," Gastroenterology, vol. 101, pp. 1020-1030, 1991.
Sellin, et al, "Inflammasomes of the intestinal epithelium," Trends in Immunology, vol. 36, No. 8, pp. 442-450, Aug. 2015.
Siegmund, Britta., "Interleukin-1β converting enzyme (caspase-1) in intestinal inflammation," Biochemical Pharmacology, vol. 64, pp. 1-8, 2002.
Siegmund, Britta., "Interleukin-18 in intestinal inflammation: friend and foe?" Immunity, 32, 2019, pp. 300-302.
Supplementary European Search Report for Application No. EP 17748124.9, dated Jul. 26, 2019 (6 pages).
Supplementary European Search Report for Application No. EP 17886282.7, dated Jun. 17, 2020 (19 pages).
Torzewski et al., "Animal Models of C-Reactive Protein," Hindawl Publishing Corporation, Mediators of Inflammation, vol. 2014, 2014, pp. 1-7.
Tseng, et al. "Activation of the NALP3 Inflammasome in Retinal Pigment Epithelial (RPE) Cells: Implications for AMD," Investigative Ophthalmology & Visual Science Apr. 2011, vol. 52, 2299 (Abstract only).
Van Der Vekens et al., Human and equine cardiovascular endocrinology: beware to compare, Cardiovascular Endocrinology 2013, vol. 2, No. 4, pp. 67-76.
Willerth et al., Tissue and Organ Engineering, 5.508.1.4.2.1 Immunostaining, Comprehensive Biomaterials, 2011, pp. 1-2.
Wong, et al., "Expert opinion on interleukin-12/23 and interleukin-23 antagonists as potential therapeutic options for the treatment of inflammatory bowel disease.," Expert Opinion Investigational Drugs 28(5), 2019, pp. 473-479 (Abstract only).
Zaki, et al., "The NLRP3 Inflammasome Protects against Loss of Epithelial Integrity and Morality during Experimental Colitis," Immunity, vol. 32, pp. 379-391, Mar. 2010.
Siegmund, et al., "IL-1β-converting enzyme (caspase-1) in intestinal inflammation." Proceedings of the National Academy of Sciences, vol. 98, No. 23, 2001, pp. 13249-13254.
European Patent Office, Extended European Search Report for Application No. 23171699.4, dated Aug. 10, 2023, 6 pages.
Japanese Patent Office, Notice of Reasons for Refusal for Japanese Application No. 2023-059927, dated Mar. 15, 2024, 9 pages.
Kiesslich, R., et al., "Identification of Epithelial Gaps in Human Small and Large Intestine by Confocal Endomicroscopy," Gastroenterology. Dec. 2007; 133(6):1769-1778.
Lim, LG, et al., "Confocal Endomicroscopy Identifies Loss of Local Barrier Function in the Duodenum of Patients with Crohn's Disease and Ulcerative Colitis," Inflamm Bowel Dis. May 2014;20(5):892-900.
[No Author Listed] Alexa Fluor® 488 Microscale Protein Labeling Kit (A30006), Molecular Probes, Invitrogen detection technologies, Revised Jul. 19, 2006, 6 pages.
Bedner, et al., "Activation of Caspases Measured in Situ by Binding of Fluorochrome-Labeled Inhibitors of Caspases (FLICA): Correlation with DNA Fragmentation," Experimental Cell Research, vol. 259, pp. 308-313, 2000.
Bullock, et al., "Biochemical and in Vivo Characterization of a Small, Membrane-Permeant, Caspase-Activatable Far-Red Fluorescent Peptide for Imaging Apoptosis," Biochemistry, vol. 46, pp. 4055-4065, 2007.
Camilleri, Michael., "Leaky gut: mechanisms, measurement and clinical implications in humans," vol. 68, No. 8, 2019, pp. 1516-1526.
Cepeniene, et al. "Selective Labeling of Lysin-Containing Biologically Active Peptides at the N-Terminus with Alexa Fluor Dye," Proceedings of the 22nd American Peptide Symposium, American Peptide Society 2011.
Chen, et al., "NOD-Like Receptors: Role in Innate Immunity and Inflammatory Disease," Annual Review of Pathology Mechanisms of Disease, vol. 4, pp. 365-398, 2009.
Chin, et al. "The role of caspase-3 in; lipopolysaccharide-mediated disruption of intestinal epithelial tight junctions," Canadian Journal of Physiology and Pharmacology, vol. 84, No. 10, Oct. 2006, pp. 1043-1050.
Chinese Office Action for Application No. 201780081439.3, dated Aug. 29, 2022, 12 pages.
Chinese Office Action for Application No. CN 201780081439.3, dated Mar. 30, 2022, 13 pages.
Davis, et al., "Pyroptosis of Intestinal Epithelial Cells Is Crucial to the Development of Mucosal Barrier Dysfunction and Intestinal Inflammation," AGA Abstracts, p. S-967 (1 page), (Apr. 2017).
Dupaul-Chicoine, et al., "Control of Intestinal Homeostasis, Colitis, and Colitis-Associated Colorectal Cancer by the Inflammatory Caspases," Immunity, vol. 32, pp. 367-378, Mar. 2010.
Dupaul-Chicoine, et al., "The Nlrp3 Inflammasome Suppresses Colorectal Cancer Metastatic Growth in the Liver by Promoting Natural Killer Cell Tumoricidal Activity," Immunity, vol. 43, pp. 751-763, Oct. 2015.
"Enzyme activity" (downloaded from URL:< Enzyme Activity (lardbucket.org)>; 2012) (Year: 2012).
European Patent Office, Communication pursuant to Article 94(3) EPC, Application No. 13834474.2. 6 pages, dated Mar. 2, 2017.
European Patent Office, Communication pursuant to Article 94(3) EPC, Application No. 17748124.9, dated Dec. 8, 2020, 5 pages.
European Patent Office, Communication pursuant to Article 94(3) EPC, Application No. 17748124.9, dated May 8, 2020, 5 pages.
European Patent Office, Communication pursuant to Rules 161 (2) and 162 EPC, Application No. 13834474.2, 3 pages, dated Apr. 29, 2015.
European Patent Office, Communication pursuant to Rules 70(2) and 70a(2) EPC, Application No. 13834474.2, 1 page, dated Jul. 26, 2016.

(56) References Cited

OTHER PUBLICATIONS

European Patent Office, Extended European Search Report for Application No. 17886282.7, dated Sep. 17, 2020, 15 pages.
European Patent Office, Extended European Search Report, Application No. 13834474.2, 12 pages, dated Jul. 7, 2016.
Examination Report for Canadian Patent Application No. 2,901,116, dated Nov. 27, 2020, 4 pages.
Examination Report for Indian Patent Application No. 1991/DELNP/2015, dated Dec. 20, 2019, 8 pages.
Fukata, et al., "The role of pattern recognition receptors in intestinal inflammation," Mucosal Immunology, vol. 6, No. 3, pp. 451-463, May 2013.
Garcia-Calvo, et al., "Inhibition of Human Caspases by Peptide-based and Macromolecular Inhibitors," The Journal of Biological Chemistry, vol. 273, No. 49, pp. 32608-32613, 1998.
Hilbi, et al., "The Interleukin 1 p-Converting Enzyme, Caspase 1, Is Activated during Shigella flexneri-Induced Apoptosis in Human Monocyte-Derived Macrophages," Infection and Immunity, vol. 65, No. 12, pp. 5165-5170, Dec. 1997.
International Preliminary Report on Patentability for International Application No. PCT/US2013/058296 along with the Written Opinion of the International Searching Authority, dated Mar. 10, 2015, 11 pages.
International Search Report along with the Written Opinion of the International Searching Authority for International Application No. PCT/US2013/058296 dated Jan. 10, 2014, 14 pages.
International Search Report along with the Written Opinion of the International Searching Authority for International Application No. PCT/US2017/068628 dated Mar. 26, 2018, 16 pages.
International Search Report and Written Opinion of the International Search Authority for Application No. PCT/US2017/016152, dated Apr. 14, 2017, 6 pages.
Invitrogen (Alexa Fluor Dyes, 2005).
Japanese Patent Office, Office Action, Application No. 2015-530160, 2 pages, dated Mar. 23, 2017 (English Translation).
Japanese Patent Office, Office Action, Application No. 2018-539357, dated Mar. 2, 2021, 13 pages.
Jarry et al., "Interleukin 1 and interleukin 1β converting enzyme (caspase 1) expression in human colonic epithelial barrier. Caspase 1 downregulation in colon cancer," Gut 1999, vol. 45, pp. 246-251.
Kanneganti T.D., "Inflammatory Bowel Disease and the NLRP3 Inflammasome," The New England Journal of Medicine, vol. 377, No. 7, pp. 694-696, Aug. 2017.
Knodler, et al., "Dissemination of invasive *Salmonella* via bacterial-induced extrusion of mucosal epithelia," Proceedings of the National Academy of Sciences, vol. 107, No. 41, pp. 17733-17738, Oct. 12, 2010.
Lee, et al. "Regulation and function of the caspase-1 in an inflammatory microenvironment," Journal of Investigative Dermatology 135(8):2012-2020, 2015.
Liu, et al., "Epithelial Cell Extrusion Leads to Breaches in the Intestinal Epithelium," Inflammatory Bowel Diseases, vol. 19, No. 5, pp. 912-921, Apr. 2013.
Liu, et al., "Epithelial Cell Extrusion Zones Observed on Confocal Laser Endomicroscopy Correlates with Immunohistochemical Staining of Mucosal Biopsy Samples", Digestive Diseases and Sciences, Springer New York LLC, US , vol. 61, No. 7, Apr. 20, 2016, pp. 1895-1902.
Liu, et al., "Mind the Gaps: Confocal Endomicroscopy Showed Increased Density of Small Bowel Epithelial Gaps in Inflammatory Bowel Disease," Journal of Clinical Gastroenterology, vol. 45, No. 3, pp. 240-245, Mar. 2011.
Liu, et al., "NLRP3 Inflammasome in Inflammatory Bowel Disease: Friend or Foe?", Digestive Diseases and Sciences, vol. 62, pp. 2211-2214, 2017.
Liu, et al., "On the Dependency of Cellular Protein Levels on mRNA Abundance," Cell vol. 165, Apr. 21, 2016, pp. 535-550.
Maier, et al., "Correlation of mRNA and protein in complex biological samples," FEBS Letters vol. 583, 2009, pp. 3966-3973.
McAlindon, et al., "Expression of interleukin 1β and interleukin 1β converting enzyme by intestinal macrophages in health and inflammatory bowel disease," Gut, vol. 42, pp. 214-219, 1998.
McAlindon, et al., "Interleukin-1β Converting Enzyme (ICE) is Expressed by Macrophages in the Lamina Propria of Active Inflammatory Bowel Disease (IBD) Mucosa," Gut, vol. 39, (Suppl. 3), p. A93, 1996.
Mehta, et al., "ATP-stimulated Release of Interleukin (IL)-β and IL-18 Requires Priming by Lipopolysaccharide and Is Independent of Caspase-1 Cleavage," The Journal of Biological Chemistry, vol. 278, No. 6, pp. 3820-3826, 2001.
Meinzer, et al. "Yersinia pseudotuberculosis Effector YopJ Subverts the Nod2/RICK/TAK1 Pathway and Activates Caspase-1 to Induce Intestinal Barrier Dysfunction," Cell Host & Microbe 11, pp. 337-351, Apr. 19, 2012.
Mennigen et al., "Probiotic mixture VSL#3 protects the epithelial barrier by maintaining tight junction protein expression and preventing apoptosis in a murine model of colitis," American Journal of Physiology—Gastrointestinal and Liver Physiology vol. 296, 2009, pp. G1140-G1149.
Menu, et al., "Atherosclerosis in ApoE-deficient mice progresses independently of the NLRP3 inflammasome," Cell Death and Disease, vol. 2, pp. e137-1-e137-4, 2011.
Mittl, et al., "Structure of Recombinant Human CPP32 in Complex with the Tetrapeptide Acetyl-Asp-Val-Ala-Asp Fluoromethyl Ketone," The Journal of Biological Chemistry, vol. 279, No. 10, pp. 6539-6547, 1997.
Monteleone, G., et al., "Bioactive IL-18 Expression is Up-Regulated in Chrohn's Disease," The Journal of Immunology 163: 143-147, 1999.

METHODS OF TREATING PATIENTS AFFLICTED WITH IRRITABLE BOWEL SYNDROME, INFLAMMATORY BOWEL DISEASE OR CHRONIC GASTROINTESTINAL FUNCTIONAL DISORDERS BASED ON ASSESSMENT OF INTESTINAL BARRIER FUNCTION

REFERENCE TO RELATED APPLICATION

This patent application is a continuation application of U.S. non-provisional application Ser. No. 16/847,134, filed Apr. 13, 2020, which is a continuation application of U.S. non-provisional application Ser. No. 16/073,212, filed Jul. 26, 2018, issued as U.S. Pat. No. 10,663,473, which is a § 371 National Phase Application of PCT Application No. PCT/US17/16152, filed Feb. 2, 2017, which claims the benefit of U.S. provisional application Ser. No. 62/290,201, filed Feb. 2, 2016 and U.S. provisional application Ser. No. 62/434,741, filed Dec. 15, 2016, the contents of each of which are hereby incorporated by reference in their entireties.

BACKGROUND

The present invention relates to the fields of biology and medicine.

It would be useful to identify inflammatory bowel disease patients who will benefit from treatment.

SUMMARY OF THE EMBODIMENTS

The invention provides methods for identifying an agent that will be beneficial to a patient with inflammatory bowel disease.

In a first aspect, the invention provides a method for identifying an agent beneficial to treat a patient with inflammatory bowel disease comprising (a) analyzing (or determining) a status of an intestinal barrier in the patient to obtain a patient status; and (b) categorizing the patient status as severe dysfunction or moderate dysfunction, wherein a patient with a patient status categorized as being severe dysfunction is identified as a patient who will benefit from treatment with an anti-TNF agent and/or an anti-IL-12/23 agent, and a patient with a patient status categorized as being moderate dysfunction is identified as a patient who will benefit from treatment with an anti-integrin agent, an anti-janus kinase agent, and/or a sphingosine-1-phosphate receptor agonist agent.

In another aspect, the invention provides a method of identifying a status of an intestinal barrier in a patient with inflammatory bowel disease, wherein the status is severe dysfunction or moderate dysfunction, comprising analyzing (or determining) the status of the intestinal barrier of the patient, wherein if said status is identified as being severe dysfunction, the method further comprises treating said patient with an anti-TNF agent and/or an anti-IL-12/23 agent, and wherein if said status is identified as having moderate dysfunction, the method further comprises treating said patient with an anti-integrin agent, an anti-janus kinase agent, and/or a sphingosine-1-phosphate receptor agonist agent.

In another aspect, the invention provides a method of treating a patient with inflammatory bowel disease, comprising (a) analyzing (or determining) the status of an intestinal barrier to determine if the status is severe dysfunction or moderate dysfunction; and (b) treating said patient with an agent, wherein: (i) if said patient is identified as having severe dysfunction, the agent is an anti-TNF agent and/or an anti-IL-12/23 agent, and (ii) if said patient is identified as having moderate dysfunction, the agent is an anti-integrin agent, an anti-janus kinase agent, and/or a sphingosine-1-phosphate receptor agonist agent.

In some embodiments of various aspects of the invention, the inflammatory bowel disease is Crohn's disease, ulcerates colitis, indeterminate colitis, or chemotherapy-induced colitis.

In various embodiments of various aspects of the invention, the status of the intestinal barrier is analyzed (or determined) by calculating or measuring an amount of activated caspase expression in intestinal epithelial cells of the intestinal barrier. In some embodiments, the activated caspase is activated caspase 1. In some embodiments, the activated caspase is activated caspase 3. In some embodiments, the activated caspase is a combination of activated caspase 1 and activated caspase 3. In some embodiments, the activated caspase is a ratio of an amount of expression of activated caspase 1 to an amount of expression of activated caspase 3.

In some embodiments, an increase in the amount of activated caspase expression by about four fold to about seven fold in the patient as compared to the amount of activated caspase expression in intestinal epithelial cells of an intestinal barrier of one or more healthy volunteers indicates that the patient status is severe dysfunction. In some embodiments, an increase in the amount of activated caspase expression by between about two fold to about four fold in the patient as compared to the amount of activated caspase expression in intestinal epithelial cells of an intestinal barrier of one or more healthy volunteers indicates that the patient status is moderate dysfunction.

In some embodiments, the status of the intestinal barrier is analyzed or determined by counting a number of gaps in histological staining of an intestinal surface at the intestinal barrier. In some embodiments, an increase in the number of gaps by about four fold to about seven fold in the patient as compared to a number of gaps in an intestinal surface at an intestinal barrier of one or more healthy volunteers indicates that the patient status is severe dysfunction. In some embodiments, an increase in the number of gaps by between about two fold to about four fold in the patient as compared to a number of gaps in an intestinal surface at an intestinal barrier of one or more healthy volunteers indicates that the patient status is moderate dysfunction.

In some embodiments of various aspects of the invention, the status of the intestinal barrier is analyzed or determined using confocal laser endomicroscopy, multi-photo confocal microscopy or fluorescent microscopy of the intestinal lining and barrier.

In some embodiments of various aspects of the invention, the anti-TNF agent is selected from the group consisting of adalimumab, infliximab, certolizumab pegol, golimumab, etanercept, and apremilast. In some embodiments, the anti-janus kinase agent is tofacitinib. In some embodiments, the anti-IL-12/23 agent is ustekinumab. In some embodiments, the sphingosine-1-phosphate receptor agonist agent is ozanimod or fingolimod. In some embodiments, the anti-integrin agent is selected from the group consisting of vedolizumab, natalizumab, and etrolizumab.

BRIEF DESCRIPTION OF THE DRAWINGS

In FIG. 3A, the white arrows point to TUNEL-positive cells (i.e., cells with nuclear fragmentation). In FIG. 3B, the white arrows point to activated caspase-3 positive cells.

DETAILED DESCRIPTION OF SPECIFIC EMBODIMENTS

Figure 1:
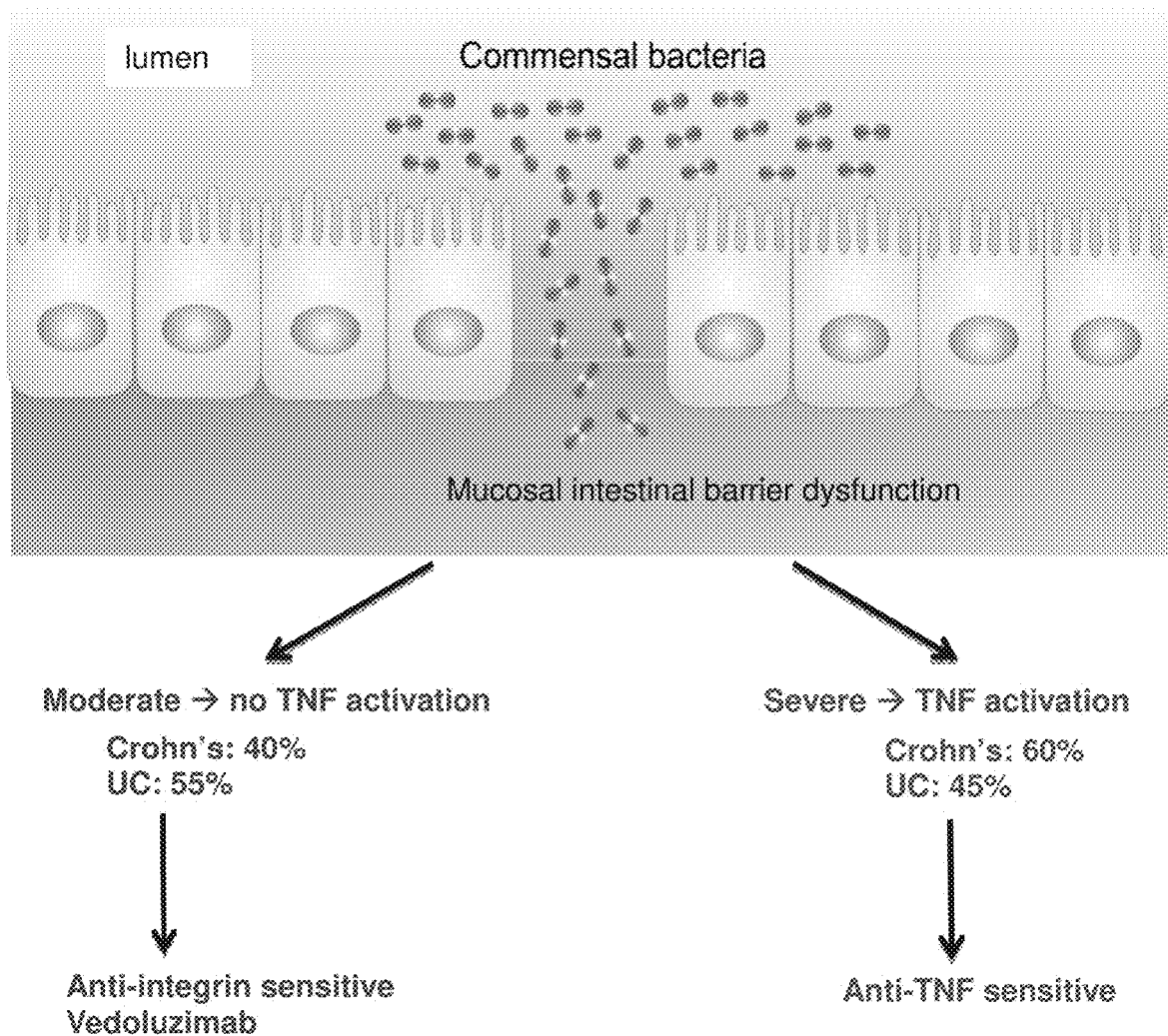
FIG. 1 is a schematic diagram showing the mucosal barrier based therapeutic approach that will optimize response to anti-integrin and anti-TNF agents.

The invention stems, in part, form the discovery that assessment of the intestinal barrier function of a patient is predictive for determining whether that patient is suffering from or is disposed to suffer from a bowel disorder such as chronic inflammatory bowel disease or irritable bowel syndrome. Such a patient thus identified may benefit from treatment with an agent that treats inflammatory bowel disease (or less commonly irritable bowel syndrome), such as an agent that blocks $\alpha_4\beta_7$ integrin (e.g., vedolizumab, a monoclonal antibody sold under the trademark Entyvio by Takeda Pharmaceuticals, Cambridge, Massachusetts) or an agent that blocks tumor necrosis factor.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Terms defined or used in the description and the claims shall have the meanings indicated, unless context otherwise requires. Technical and scientific terms used herein have the meaning commonly understood by one of skill in the art to which the present invention pertains, unless otherwise defined. Any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The intestinal epithelium is a single-cell layer that constitutes the largest and most important barrier against the external environment. Thus, this intestinal epithelial layer shall be referred to herein as an "intestinal barrier". The intestinal barrier acts as a selectively permeable barrier, permitting the absorption of nutrients, electrolytes, and water while maintaining an effective defense against intraluminal toxins, antigens, and enteric flora. The lining of the intestine which makes up the intestinal barrier undergoes continuous physiologic renewal: stem cells located at the base of the crypts mature and migrate up the villi. The mature epithelial cells are eventually shed at the tip of the villi.

Studies published over the past two decades have convincingly shown that intestinal barrier disruption plays a crucial role in the pathogenesis of intestinal inflammation and in the severity of inflammatory bowel disease (IBD), such as Cohn's disease (CD) and ulcerative colitis (UC). Crohn's disease is a chronic relapsing inflammatory bowel disorder (IBD). Clinical relapse occurs in 30-60% of patients within one year of medically induced remission. Studies over the past two decades have convincingly demonstrated that barrier disruption plays a significant and important role in the pathogenesis of intestinal inflammation and in the severity of Crohn's disease.

Methods for detecting intestinal cell barrier dysfunction have been described (see, e.g., PCT Publication No. WO2014/039699 and US patent publication no. US 2015/0202329, both incorporated by reference herein their entireties). Barrier disruption not only exposes the subepithelial immune system to resident microbes but also induces the secretion of TNF-α and other pro-inflammatory cytokines (Neish A S: Microbes in gastrointestinal health and disease. Gastroenterology 2009, 136(1):65-80). The cytokine secretion in turn induces more shedding of epithelial cells and promotes further inflammation and barrier dysfunction (Watson A J, Duckworth C A, Guan Y, Montrose M H: Mechanisms of epithelial cell shedding in the Mammalian intestine and maintenance of barrier function. *Annals of the New York Academy of Sciences* 2009, 1165:135-142).

Older assays for barrier function such as the lactulose/mannitol test (May G R, Sutherland L R, Meddings J B: Is small intestinal permeability really increased in relatives of patients with Crohn's disease? Gastroenterology 1993, 104 (6):1627-1632) have not been useful clinically, because the size of the sugar molecules used in the test (about $10^{-10}$ m) are not reflective of those of the resident microbes (about $10^{-6}$ n).

More recently, the advent of confocal laser endomicroscopy (CLE) has enabled the real-time assessment of mucosal barrier function in vivo (Kiesslich R et al., "Identification of epithelial gaps in human small and large intestine by confocal endomicroscopy. *Gastroenterology* 2007, 133(6): 1769-1778; Liu J J, et al., "Epithelial cell extrusion leads to breaches in the intestinal epithelium", *Inflammatory bowel diseases* 2013, 19(5):912-921). The density of epithelial gaps (also known as extrusion zones) in the intestinal surface as observed by CLE has been shown to be a surrogate marker for mucosal barrier function (Liu J J, et al., "Mind the gaps: confocal endomicroscopy showed increased density of small bowel epithelial gaps in inflammatory bowel disease," *Journal of clinical gastroenterology* 2011, 45(3):240-245). Gap density is defined as the total number of epithelial gaps per a set number of total cells (e.g., 1000 cells). The epithelial gaps or extrusion zones may be potential entry sites for luminal microbes into the host. Epithelial gap density has also been validated by conventional light microscopy as a measure of epithelial cell extrusion (Liu J J, et al., "Epithelial gaps in a rodent model of inflammatory bowel disease: a quantitative validation study," *Clinical and Translational Gastroenterology* 2011, 2:e3). The epithelial gap density—a validated measure of epithelial cell extrusion against conventional light microscopy (Liu J J, et al., "Epithelial gaps in a rodent model of inflammatory bowel disease: a quantitative validation study". *Clinical and Translational Gastroenterology* 2011, 2:e3]—is increased in nearly half of UC patients (Turcotte J F et al., "Breaks in the wall: increased gaps in the intestinal epithelium of irritable bowel syndrome patients identified by confocal laser endomicroscopy (with videos)", *Gastrointestinal Endoscopy* 2013, 77(4):624-630) and is a linear predictor of moderate to severe flare within a one-year follow-up period (Turcotte J F, et al., "Increased epithelial gaps in the small intestine are predictive of hospitalization and surgery in patients with inflammatory bowel disease," *Clinical and Translational Gastroenterology* 2012, 3:e19).

Epithelial gaps appear to be potential sites for the entry of luminal microbes into the host (Liu J J, et al.: Epithelial cell extrusion leads to breaches in the intestinal epithelium. *Inflammatory Bowel Diseases* 2013, 19(5):912-921). The severity of mucosal barrier dysfunction to luminal microbes as measured by gap density on CLE therefore, is likely to be predictive of disease relapse. Elevated epithelial gap densities are found in 60% of Crohn's disease (CD) patients and in 45% of ulcerative colitis (UC) patients (Turcotte J F, et al., "Breaks in the wall: increased gaps in the intestinal epithelium of irritable bowel syndrome patients identified by confocal laser endomicroscopy (with videos)," *Gastrointestinal Endoscopy* 2013, 77(4):624-630) and are reported to be a linear predictor of moderate to severe flare within a one-year follow-up period (Turcotte J F et al., "Increased epithelial gaps in the small intestine are predictive of hospitalization and surgery in patients with inflammatory bowel disease," *Clinical and Translational Gastroenterology* 2012, 3:e19). Moreover, gap densities determined by CLE correlated strongly with the levels of activated caspases expressed in mucosal biopsy samples as determined by quantitative analysis of immunohistochemical staining (unpublished). The correlation between gap density on CLE and mucosal biopsy analysis will enable the use of intestinal biopsy samples for barrier function analysis.

A recent study of molecular imaging using CLE in the intestine of Crohn's patients revealed that careful patient selection based on the status of their mucosal TNF receptor expression can increase the clinical response rate to anti-TNF antibody therapy to over 90% (Atreya R, et al., "In vivo imaging using fluorescent antibodies to tumor necrosis factor predicts therapeutic response in Crohn's disease," *Nature Medicine* 2014, 20(3):313-318). This result highlights the role of mucosal TNF levels in determining the response rate to biologic agents. IBD patients with higher gap densities have been found to display increased mucosal pro-inflammatory cytokine levels in their mucosal biopsy specimens (Liu J J et al., "Epithelial cell extrusion leads to breaches in the intestinal epithelium," *Inflammatory bowel diseases* 2013, 19(5):912-921).

The present invention stems, in part, from the discovery that IBD patients with severe barrier dysfunction resulting in enhanced mucosal TNF levels will have a beneficial response to an agent that treats bowel disorders. Such agents that treat IBD include, without limitation, anti-TNF agents and agents that inhibit interleukin-12 and interleukin-23. CD patients with enhanced TNF levels were found to display a greater than 90% response rate to anti-TNF therapy (Atreya et al., "In vivo imaging using fluorescent antibodies to tumor necrosis factor predicts therapeutic response in Crohn's disease." *Nature Medicine* 2014, 20(3):313-318).

Patients with severe barrier dysfunction will also have a beneficial response (i.e., will respond favorably) to an agent that inhibits interleukin-12 and interleukin-23 (IL-12 and IL-23, respectively). IL-12 and IL-23 share a common p40 subunit. IL-12 is made up of the IL-12/23p40 and IL-12p35 subunits, and IL-23 comprises IL-23p19 and IL-12/23p40. Such an agent includes, without limitation, ustekinumab, which is sold under the trademark Stelara® by Johnson & Johnson Corp., New Jersey, USA. An agent that inhibits IL-12 and IL-23 will be referred to herein as an "anti-IL12/23 agent)

Conversely, those patients with lesser mucosal barrier dysfunction, and, in some embodiments, without increased mucosal TNF activity, only had a 10% response rate to anti-TNF therapy. In other words, patients with a moderate barrier dysfunction did not have a beneficial response to anti-TNF therapy. Instead, these patients are more likely to have a beneficial response to anti-integrin therapy. In Crohn's patients with lower (i.e., "moderate") range of gap density (e.g., 3% or less), the response rate to anti-integrin therapy was found to be 100% at the two-year follow-up examination (unpublished).

Patients with moderate intestinal barrier dysfunction (e.g., without increased mucosal TNF activity) will also have a beneficial response to sphingosine-1-phosphate receptor agonists, such as fingolimod (tradename Gilenya®, available from Novartis AG Corp. Switzerland) or ozanimod (developed by Receptos, Inc. and currently available from Celgene, Inc.), and/or an agent that inhibits a janus kinase family member, such as tofacitinib (tradenames Xeljanz® and Jakvinus®, available from Pfizer, Inc.).

As used herein, by the term "anti-TNF therapy" is meant the administration, to a patient (e.g., a human patient), of an agent that inhibits tumor necrosis factor (referred to as TNF or TNF alpha). Several such anti-TNF agents are commercially available and have been approved for use in human patients in the USA by the U.S. Food and Drug Administration. Any anti-TNF agent, where a biological or a small molecule, is contemplated in the invention. In some embodiments, anti-TNF agent may be adalimumab (trade name Humira®, sold by Abbie, Chicago, Illinois, USA), infliximab (trade name Remicade®, sold by Janssen Biotech, Inc., Horsham, Pennsylvania, USA), certolizumab pegol (trade name Cimzia®, sold by UCB S.A., Brussels, Belgium), golimumab (trade name Simponi®, sold by Janssen Biotech, Inc., Horsham, Pennsylvania, USA), or etanercept (trade name Enbrel®, sold by Amgen and Pfizer). Yet additional non-limiting anti-TNF agents are those that inhibit production of TNF (e.g., TNF-alpha) by cells by, for example, inhibiting enzymes (e.g., protein kinases) in the cells to inhibit their production of TNF. One such anti-TNF agent that acts to prevent TNF-alpha production is apremilast (trade name Otezla, sold by Celgene Corp, New Jersey, USA).

As used herein, by the term "anti-integrin therapy" is meant the administration, to a patient, of an agent that inhibits an integrin from forming an adhesion with its natural target. Thus, an anti-integrin agent, when bound to the integrin, partially or completely prevents the integrin from binding its target. Integrins are family of transmembrane receptors that appear on a variety of cells. They are heterodimers comprised of two chains—an alpha chain and a beta chain. In mammals, there are eighteen alpha chains and eight beta chains, so a particular integrin may be referred to by which alpha chain and which beta chain it has. Some non-limiting examples of integrins are the $\alpha_1\beta_1$ integrin (also called VLA-1), the $\alpha_4\beta_7$ integrin (also called LPAM-1), and the $\alpha_1\beta_2$ integrin (also called LFA-1). An anti-integrin agent is an agent that inhibits (i.e., blocks) any integrin family member (i.e., inhibits one or more integrin family member).

In some embodiments, the anti-integrin agent is vedolizumab which targets LPAM-1 (the trade name of vedolizumab is Entyvio®, and vedolizumab is sold by Millennium Pharmaceuticals (Cambridge, Massachusetts, USA), a subsidiary of Takeda Pharmaceuticals, Japan). In some embodiments, the anti-integrin agent is natalizumab which targets alpha 4 chain integrin(s). The trade name of natalizumab is Tysabri®, and natalizumab is sold by BioGen Idec (Cambridge, Massachusetts, USA) and Elan (Dublin, Ireland). In some embodiments, the anti-integrin agent is etrolizumab (available from Genentech, South San Francisco, California, USA) which targets the β7 chain integrin(s) (e.g., integrins $\alpha_4\beta_7$ and $\alpha E\beta 7$). Additional anti-integrin agents are described in Kawamoto et al., Autoimmune Diseases, vol. 2012, Article ID 357101, herein incorporated by reference.

It shall be understood that the amount of any agent (e.g., anti-TNF agent or anti-integrin) that administered to a patient to "treat" that patient will be administered in a therapeutically effective amount, as determined by ordinarily skilled physicians, pharmacologists, and toxicologists, that make take into account the weight and age of the patient. In any event, where the drug has been approved by a regulatory authority (e.g., the U.S. Food and Drug Administration), a therapeutically effective amount of anti-TNF agent is an amount approved by the regulatory authority.

Of course, the route of administration can be by any route and will be determined based on the agent and the patient. For example, a small molecule such as apremilast may be administered orally, while a biological such as etanercept may be administered by subcutaneous injection. All other routes of administration of a therapeutically effective amount of an agent to treat an IBD patient are contemplated herein and include, without limitation, parenteral (e.g., intravenous, intrathecal, subcutaneous) or enteral (e.g., orally or rectally) or other routes (e.g., intranasal, intradermal, intravitreal, subcutaneous, transdermal, topical, intraperitoneal, intravaginal, and intramuscular).

The invention is based, in part, on the discovery that the mucosal intestinal barrier status while inflammatory bowel disease (IBD) patients are on IBD therapy is predictive of clinical and endoscopic remission over time in response to that therapy (e.g., treatment with an anti-TNF agent). Thus, the invention is based, in part, on the discover that determining the mucosal intestinal barrier function status in patients with inflammatory bowel disease (IBD) is an important tool for predicting therapeutic response to a therapeutic agent, such as an anti-TNF agent, an anti-integrin agent, or an anti-IL-12 and IL-23 agent (e.g., ustekinumab). First of all, IBD patients with higher gap densities have higher mucosal pro-inflammatory cytokine levels (see Liu J J, et al: "Epithelial cell extrusion leads to breaches in the intestinal epithelium." *Inflammatory bowel diseases* 2013, 19(5):912-921). Second, the highest rates of response to biologic therapy for Crohn's disease are seen in post-operative patients, with over 90% endoscopic remission rate at one year (see Regueiro M, Schraut W, Baidoo L, Kip K E, Sepulveda A R, Pesci M, Harrison J, Plevy S E: Infliximab prevents Crohn's disease recurrence after ileal resection. *Gastroenterology* 2009, 136(2):441-450 e441; quiz 716). Third, prominent barrier dysfunction was observed at the anastomotic site in animal models of ileal resection (unpublished).

It has been discovered that normalization of mucosal intestinal barrier function for IBD patients (Crohn's disease, ulcerative colitis, indeterminate colitis, or chemotherapy-induced colitis) on IBD therapy to healthy control (e.g., from healthy volunteers) levels is predictive of clinical and endoscopic remission for a significant period of time (e.g., one year). Correspondingly, abnormal mucosal intestinal barrier function on biologic therapy is predictive of lack of clinical response and disease relapse.

Therefore, barrier dysfunction is a potent predictor of therapeutic response to an IBD therapy, such as administration of an anti-TNF agent or an anti-integrin agent in IBD patients.

Accordingly, in a first aspect, the invention provides a method for identifying an agent beneficial to treat a patient with inflammatory bowel disease comprising (a) analyzing (or determining) a status of an intestinal barrier in the patient to obtain a patient status; and (b) categorizing the patient status as severe dysfunction or moderate dysfunction, wherein a patient with a barrier status categorized as being severe dysfunction is identified as a patient who will benefit from treatment with an agent selected from the group consisting of an anti-TNF agent, an anti-IL-12/23 agent, and a combination thereof; while a patient with a patient barrier status categorized as being moderate dysfunction is identified as a patient who will benefit from treatment with an agent selected from the group consisting of an anti-integrin agent, an anti-janus kinase agent a sphingosine-1-phosphate receptor agonist agent, a combination of two or more of an anti-integrin agent, an anti-janus kinase agent a sphingosine-1-phosphate receptor agonist agent.

In another aspect, the invention provides a method of identifying a status of an intestinal barrier in a patient with inflammatory bowel disease, wherein the status is severe dysfunction or moderate dysfunction, comprising analyzing (or determining) the status of the intestinal barrier of the patient, wherein if said status is identified as being severe dysfunction, the method further comprises treating said patient with an agent selected from the group consisting of an anti-TNF agent, an anti-IL-12/23 agent, and a combination thereof, and wherein if said status is identified as having moderate dysfunction, the method further comprises treating said patient with an agent selected from the group consisting of an anti-integrin agent, an anti-janus kinase agent a sphingosine-1-phosphate receptor agonist agent, a combination of two or more of an anti-integrin agent, an anti-janus kinase agent a sphingosine-1-phosphate receptor agonist agent.

In another aspect, the invention provides a method of treating a patient with inflammatory bowel disease, comprising (a) analyzing (or determining) the status of an intestinal barrier to determine if the status is severe dysfunction or moderate dysfunction; and (b) treating said patient with an agent, wherein: (i) if said patient is identified as having severe dysfunction, the agent is selected from the group consisting of an anti-TNF agent, an anti-IL-12/23 agent, and a combination thereof, and (ii) if said patient is identified as having moderate dysfunction, the agent is selected from the group consisting of an anti-integrin agent, an anti-janus kinase agent a sphingosine-1-phosphate receptor agonist agent, a combination of two or more of an anti-integrin agent, an anti-janus kinase agent a sphingosine-1-phosphate receptor agonist agent.

The invention stems, in part, from the discovery that the status of the intestinal barrier of an inflammatory bowel disease patient can reveal which agent would be most beneficial in treating the patient. As used herein, by "beneficial" is meant that the IBD symptoms of the patient are alleviated when the patient is treated (e.g., by oral administration) of a therapeutically effective amount of an anti-TNF or an anti-integrin agent. The patient thus treated is referred to as a patient who has a beneficial response to the treatment.

Symptoms of IBD are well known and include, without limitation, diarrhea, fever (e.g., low-grade fever), abdominal pain and cramping, blood in the stool (hematochezia), bleeding ulcers, bloating, bowel obstruction, unintended weight loss, and anemia. Crohn's disease, ulcerates colitis, indeterminate colitis, and chemotherapy-induced colitis are all forms of inflammatory bowel disease. Note that chemotherapy-induced colitis, unlike other forms of IBD, is not predictable, as it occurs in a minority (less than 30%) of patients who have been treated with a chemotherapeutic drug such as checkpoint inhibitors.

In some embodiments, the status of the intestinal barrier is determined by measuring or calculating the amount of activated caspase expressed in intestinal epithelial cells at the intestinal surface of the intestinal barrier. For example, the amount of activated caspase can be determined by staining a sample (e.g., a biopsy sample) from the patient with a detectably labeled antibody that specifically binds to an activated caspase molecule (e.g., activated caspase 1 or activated caspase 3). The amount of activated caspase can also be determined by staining a sample from the patient with a detectably labeled peptide that binds to activated caspase. It should be noted that by being detectably labeled, the peptide or antibody can be directly labeled (e.g., with a fluorescent label or chromatogenic tag) or can be detected by being bound during secondary staining with an detectably labeled secondary antibody (e.g., the anti-caspase antibody is a murine monoclonal antibody and the secondary antibody is a fluorescently labeled rabbit anti-mouse antibody).

In some embodiments, the activated caspase is activated caspase 1. In some embodiments, the activated caspase is activated caspase 3. In some embodiments, the activated caspase is a combination of activated caspase 1 and activated caspase 3. In some embodiments, the activated caspase is a ratio of an amount of expression of activated caspase to an amount of expression of activated caspase 3.

Typically, intestinal epithelial cells at the intestinal barrier of people who do not have intestinal diseases (e.g., do not have IBD or IBS symptoms) expresses low levels of activated caspases (e.g., low levels of activated caspase 1 or activated caspase 3). Such people who do not have IBD may be referred to as a healthy volunteer. Accordingly, in some embodiments, an amount of activated caspase expression in that patient that is about four fold to about seven fold higher than the amount of activated caspase expression in intestinal epithelial cells of an intestinal barrier of one or more healthy volunteers indicates that the patient status is severe dysfunction. In some embodiments, an amount of activated caspase expression in that patient that is about 4 fold to about 7 fold higher than the amount of activated caspase expression in intestinal epithelial cells of an intestinal barrier of one or more healthy volunteers indicates that the patient status is severe dysfunction. In some embodiments, an amount of activated caspase expression in that patient that is about 5 fold to about 6.5 fold higher than the amount of activated caspase expression in intestinal epithelial cells of an intestinal barrier of one or more healthy volunteers indicates that the patient status is severe dysfunction.

In some embodiments, an amount of activated caspase expression in the patient that is between about 1.5 fold to about 4.5 fold higher than the amount of activated caspase expression in intestinal epithelial cells of an intestinal barrier of one or more healthy volunteers indicates that the patient status is moderate dysfunction and is not severe dysfunction. In some embodiments, an amount of activated caspase expression in the patient that is between about 2 fold to about 4.5 fold higher than the amount of activated caspase expression in intestinal epithelial cells of an intestinal barrier of one or more healthy volunteers indicates that the patient status is moderate dysfunction and is not severe dysfunction. In some embodiments, an amount of activated caspase expression in the patient that is between about 2 fold to about 4 fold higher than the amount of activated caspase expression in intestinal epithelial cells of an intestinal barrier of one or more healthy volunteers indicates that the patient status is moderate dysfunction and is not severe dysfunction.

The expression level amount of activated caspase in a healthy volunteer can be pooled and averaged with other healthy volunteers. For example, if you have two healthy volunteers, and one has no activated caspase 1 expression and the other has 1.0% activated caspase 1 expression, the average is 0.5% activated caspase 1 expression in the intestinal epithelial cells of the intestinal barriers of healthy volunteers.

In some embodiments, the amount of activated caspase expression in intestinal epithelial cells of an intestinal barrier of a healthy volunteer is 0.5%. Thus, if a patient has 1.5% activated caspase 1 expression (i.e., has 1.5 out of 100 intestinal epithelial cells expressing activated caspase 1), that patient will be categorized as having moderate dysfunction of the status of his intestinal barrier. Conversely, if a patient has 5.5% activated caspase 1 expression (i.e., has 5.5 out of 100 intestinal epithelial cells expressing activated caspase 1), that patient will be categorized as having severe dysfunction of the status of his intestinal barrier.

Note that the amount of activated caspase expressed by a healthy volunteer will depend upon several factors including the reagent used to detect the activated caspase (e.g., the peptide inhibitor, Ac-YVAD (tyr-val-ala-asp)-CMK, from Enzo described below that inhibits activated caspase 1 or an antibody that specifically binds to activated caspase 1 such as the antibody from Cell Signaling Technology, Inc. described below).

In some embodiments, the amount of activated caspase expression in intestinal epithelial cells of an intestinal barrier of a healthy volunteer is 1%. Thus, if a patient has 3% activated caspase 1 expression (i.e., has 1.5 out of 100 intestinal epithelial cells expressing activated caspase 1), that patient will be categorized as having moderate dysfunction of the status of his intestinal barrier because the patient has a 2 fold higher expression of activated caspase 1 than the healthy volunteer. Correspondingly, if a patient has 6% activated caspase 1 expression (i.e., has 6 out of 100 intestinal epithelial cells expressing activated caspase 1), that patient will be categorized as having severe dysfunction of the status of his intestinal barrier because the patient has a 6 fold higher expression of activated caspase 1 than the healthy volunteer.

In some embodiments, the amount of activated caspase expression in intestinal epithelial cells of an intestinal barrier of a healthy volunteer is approximately 0.5%. Thus, if a patient has 1.5% activated caspase 1 expression (i.e., has 1.5 out of 100 intestinal epithelial cells expressing activated caspase 1), that patient will be categorized as having moderate dysfunction of the status of his intestinal barrier because the patient has a 3 fold higher expression of activated caspase 1 than the healthy volunteer. Correspondingly, if a patient has 3.0% activated caspase 1 expression (i.e., has 3 out of 100 intestinal epithelial cells expressing activated caspase 1), that patient will be categorized as having severe dysfunction of the status of his intestinal barrier because the patient has a 6 fold higher expression of activated caspase 1 than the healthy volunteer (i.e., 3% is 6 fold higher than 0.5%).

Where there is no number or percentage value available for "the amount of activated caspase expression in intestinal epithelial cells of an intestinal barrier of one or more healthy volunteers", that amount shall understood to be in the range of about 0.5 to 1.0 cells out of 100, or 0.5% to 1.0% expression.

In some embodiments, the status of the intestinal barrier is determined by counting a number of gaps in routine histological staining of the intestinal lining. For example, the residual spaces left in between cells in the intestinal surface after extrusion of epithelial cells, also called extrusion zones, can be counted on well preserved intestinal specimens and normalized to the total number of epithelial cells to reflect the barrier status. The samples can be stained using conventional histologic staining techniques, including but not limited to hematoxylin and eosin stain, alcian blue and nuclear fast red.

In some embodiments, the status of the intestinal barrier is determined by measuring gap density (i.e., number of gaps) using confocal endomicroscopy of the intestinal surface. For example, the intestinal samples can be stained with a nuclear (such as DAPI) stain and cytoskeletal (e.g., actin) stain and imaged using multi-photon confocal microscopy ex-vivo.

Ordinarily, a healthy volunteer will have very little intestinal barrier gaps, and so that number of gaps in a healthy volunteer is ordinarily under 0.5 gaps per 100 intestinal epithelial cells.

However, where there is no number or percentage value available for the number of gaps or the gap density of one or more healthy volunteers, that amount shall understood to be approximately 0.5 gaps per 100 intestinal cells, or approximately 0.5%.

In some embodiments, the mucosal (or intestinal) barrier status or the degree of intestinal barrier dysfunction can be characterized by a combination stain for activated caspase-1 and/or activated caspase-3 of intestinal epithelial cells, and anti-CD3 of intraepithelial lymphocytes. The total number of intestinal epithelial cells can be quantitated using nuclear stains (e.g., DAPI). The staining methods are detailed in Protocol A "Staining protocol for paraffin-embedded mucosal biopsy samples" below.

The degree of intestinal barrier dysfunction can be derived by either the total number of activated caspase-1 positive cells normalized to the total number of intestinal epithelial cells (e.g., as determined by nuclear stain); or a relative ratio of activated caspase-1 positive to activated caspase-3 positive cells, or a combination of activated caspase-1 positive and activated caspase-3 positive cells normalized to the total number of intestinal epithelial cells.

The intestinal barrier status or the degree of barrier dysfunction can also be characterized by a combination stain for TUNEL stain which will stain positive for both activated caspase-1 and activated caspase-3 epithelial cells, minus the activated caspase-3 positively stained cells; with or without anti-CD3 stain for intraepithelial lymphocytes. The total number of intestinal epithelial cells can be quantitated using nuclear stains, e.g. DAPI. The staining methods are detailed in protocol B "TUNEL staining protocol for paraffin-embedded mucosal biopsy samples using commercially-available staining kits", below.

In some embodiments, the intestinal (i.e., mucosal) barrier dysfunction can alternatively be characterized by staining for active interleukin 1-beta (IL-1β) and/or IL-18, both of which are surrogate markers of activated caspase-1. Antibodies that specifically bind to active (i.e., mature) interleukin 1-beta (IL-1β) and antibodies that specifically bind to IL-18 are known (see, e.g., Cleaved-IL-1β (Asp116) (D3A3Z) Rabbit mAb #83186, Cell Signaling Technology, Inc., Danvers, Massachusetts, USA, and Anti-IL18 antibody (ab71495), Abcam, Cambridge, Massachusetts, USA).

In vivo, the intestinal surface may be stained with intravenous dye (e.g., fluorescein) with or without a nuclear stain (e.g., acriflavine), and imaged using confocal laser endomicroscope. Gap density on confocal laser endomicroscopy is a validated measure of extrusion zones.

The status of the intestinal barrier is significantly compromised in inflammatory bowel disease (IBD) patients as compared to the status of an intestinal barrier from a healthy volunteer (e.g., a person, aged 18 to 70) who does not have gastrointestinal symptoms.

It will be understood that each therapeutic agent (or, for example, each target of a group of therapeutic agents) may present itself with its own specific profile for caspase 1 and/or caspase 3 staining to show optimal therapeutic efficacy. For example, for an anti-TNF agent (depending upon which agent), one non-limiting profile for positive caspase-1 stain is estimated to be above between about 4 to 7 positive activated caspase-1 cells per 100 intestinal epithelial cells on the biopsy samples, or between about 4% to about 7%, depending on the specific anti-TNF, as well as the disease condition (e.g., Crohn's disease, ulcerative colitis, or indeterminate colitis).

In some embodiments, the anti-TNF agent is selected from the group consisting of adalimumab, infliximab, certolizumab, pegol, golimumab, and etanercept. As described below, the therapeutic response rate to an anti-TNF agent in patients with inflammatory bowel disease (e.g., Crohn's patients or ulcerative colitis) is expected to be above 70, when the criteria above for severe dysfunction is met (e.g., positively stained cells or gap density of over between about 4% to 7% for Crohn's disease or ulcerative colitis).

In some embodiments, the anti-integrin agent is selected from the group consisting of vedolizumab, natalizumab, and etrolizumab. As described below, the response rate to these anti-integrin agents in IBD patients (e.g., Crohn's or ulcerative colitis patients) is expected to be above about 70 to 80% when the criteria for moderate barrier dysfunction is met, (e.g., positively stained cells or gap density of less than about 4%).

The following examples are not meant to limit the invention in any way.

Staining Protocols A and B

In general, staining (i.e., contacting a sample with a binding agent, where the binding can be detected) can be performed as follows.

Protocol A: Staining Protocol for Paraffin-Embedded Mucosal Biopsy Samples

Step I. Deparaffinization

Place the slides in a rack, and perform the following sequential washes in Coplin jars or other container:

Wash 1. Xylene: 2×5 minutes
Wash 2. 100% ethanol: 2×5 minutes
Wash 4. 95% ethanol: 3 minutes
Wash 5. 70% ethanol: 3 minutes
Wash 6. 50% ethanol: 3 minutes
Wash 7. Distilled H$_2$O: 2×3 minutes Keep the slides in the distilled water until ready to perform antigen retrieval. In some embodiments, do not allow the slides to dry from this point onwards, as drying out may cause non-specific antibody binding and therefore high background staining on the tissue.

Step II. Antigen Retrieval

1. Pre-heat a water bath and antigen retrieval solution (10 mM sodium citrate buffer) to 95° C.

The 10 mM Sodium Citrate Buffer is 10 mM sodium citrate, 0.05% Tween 20, pH 6.0, and is made as follows:

Tri-sodium citrate (dihydrate) 2.94 g
Distilled water 1000 ml
Mix to dissolve. Adjust pH to 6.0 with 1N HCl.
Add 0.5 ml Tween 20, mix well, and store at 4° C.

2. Place slides in pre-heated antigen retrieval solution (enough to cover the slides by about 1 to about 8 centimeters). As glass containers may crack in the heat, in some embodiments, glass containers are not used. In some embodiments, a plastic tupperware container with a lid to prevent evaporation may be used. In some embodiment, an empty box with a lid (e.g., a box that used to hold pipet tips for a micropipetter) may be used. In embodiments, a weight is added on the cover of the container to prevent the container from floating around.

3. Incubate the slides for 20 minutes at 95° C.

4. When 20 minutes have elapsed, remove the container and slides from the water bath. Allow the slides to cool at room temperate, still immersed in the antigen retrieval solution, before removing them from the container.

5. Continue to the immunohistochemical staining protocol (i.e., Step III).

Step III. Immunostaining

All incubations should be carried out in a humidified chamber to avoid drying of the tissue.

A shallow, plastic box with a sealed lid and wet tissue paper in the bottom works well. In some embodiments, the slides do not directly contact the paper. In some embodiments, the slides can lay flat. In some embodiments, the slides are positions so that the reagents do not drain off.

1. Wash slides in 1×PBS (phosphate buffered saline) with 0.025% Triton X-100 for 5 minutes with gentle agitation. Repeat with a second wash for a total of 2 washes.

2. Remove slides from wash buffer and dry excess liquid from slides using a Kimwipe or other delicate task wipe with low lint and low electrostatic discharge. Use a PAP pen or other similar pen to draw a circle around the tissue to create a hydrophobic barrier around the sample.

3. Pipet approximately 100 uL of blocking solution onto the tissue, ensuring that the tissue section is completely covered, and incubate the tissues at room temperate for 2 hours. The Blocking solution contains: 1×PBS with 10% normal goat serum and 1% BSA (bovine serum albumin)

4. Use a Kimwipe to blot out any excess blocking solution from the tissue and add approximately 100 uL of primary antibody solution to each slide. Incubate overnight at 4° C. The Primary antibody solution contains 1×PBS with 1% BSA with Caspase-1 p20 antibody at 1:250 dilution (using, for example, the Cleaved caspase-1 (Asp297)(D57A2) rabbit mAb available from Cell Signaling Technologies (Danvers, Massachusetts), cat #4199) and with CD3e antibody at 1:100 dilution (using, for example, the CD3e/CD3 epsilon antibody (SPV-T3b) human, raised in mouse; Invitrogen (Carlsbad, California) cat #07-0303)

Note that staining of activated caspase 1 can also be accomplished by immunoblotting with a peptide inhibitor, such as the Ac-YVAD (tyr-val-ala-asp)-CMK inhibitor commercially available from Enzo Life Sciences, Farmingdale, New York, and described in PCT Publication No. WO2014/039699 and US patent publication no. US 2015/0202329, both incorporated by reference herein their entireties). The peptide Ac-YVAD-CMK (Ac-Tyr-Val-Ala-Asp-chloromethylketone) is a cell permeable, irreversible inhibitor of capspase-1.

5. Drain off excess primary antibody solution and wash the slides in 1×PBS for 5 minutes with gentle agitation. Repeat twice for a total of 3 washes.

6. Pipet approximately 100 uL of secondary antibody solution onto the tissues and incubate at room temperature (e.g., 25° C.) for 1 hour in the dark. The Secondary antibody solution contains 1×PBS with 1% BSA with Goat anti-rabbit AlexaFluor 488 at 1:3000 dilution (using, for example, the Goat anti-rabbit (H+L) Superclonal secondary antibody, AlexaFluor conjugate 488; Invitrogen, cat #PIA27034) and with Goat anti-mouse AlexaFluor 555 at 1:3000 dilution (using, for example, the Goat anti-mouse IgG (H+L), AlexaFluor conjugate 555; Invitrogen, cat #A21424

7. Blot off excess antibody solution and wash the slides in 1×PBS for 5 minutes, with gentle agitation. Repeat once for a total of two washes. Perform washes in the dark.

8. Incubate slides in 1×PBS containing 0.3 ug/mL (0.654 nM) DAPI (4',6-Diamidino-2-Phenylindole, Dilactate), commercially available for example, from Molecular Probes, cat #D3571 for 10 minutes with gentle agitation in the dark. For example, 12 uL of 5 mg/mL DAPI stock into 200 mL PBS can be used for a final wash+stain in one step.

9. Drain off excess liquid, wipe around the sections with tissue paper, and mount coverslips onto the tissue. This can be done using a mounting agent such as, for example, ProLong Diamond Antifade Mountant (Molecular Probes (Eugene, Oregon), cat #P36970). Allow the slides to cure (i.e., the tissue with the mounting agent sets and hardens with time) overnight at room temperature in the dark before imaging.

Slides are imaged using either multi-photon microscopy or fluorescent microscopy, using wavelengths corresponding to the fluorochrome used. Note that confocal laser endomicroscopy can be performed on patient samples during the time of endoscopy, while multi-photon confocal microscopy or fluorescent microscopy can be done on the slides stained with immunohistochemical (IHC) stains (e.g., using labeled monoclonal antibodies specific for activated caspase 1).

Figure 2:
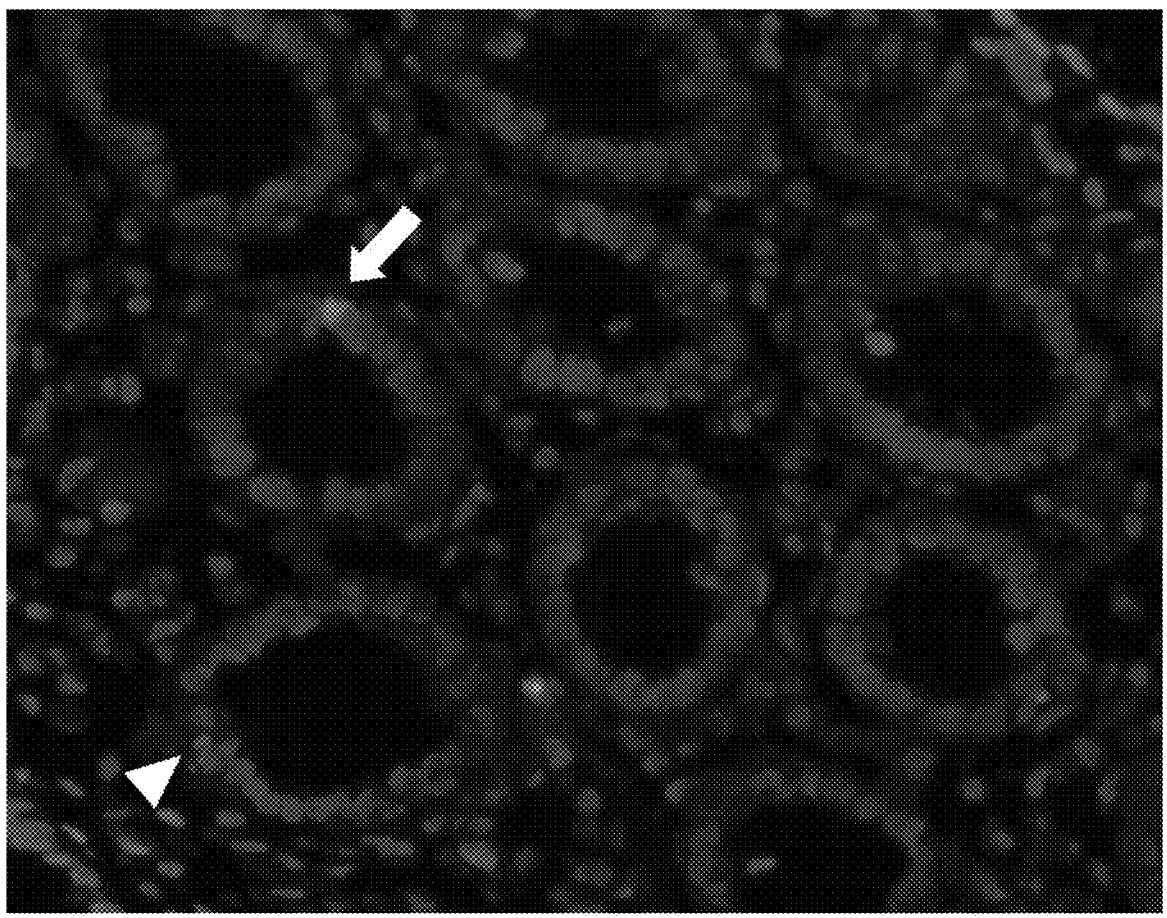
FIG. 2 is a photographic image showing staining for activated caspase 1 in intestinal epithelial cells (IECs). The white arrow points to IECs staining positive for activated caspase 1, and the white arrowhead points to intra-epithelial lymphocytes staining positive for both activated caspase 1 and for CD3 (a T cell marker).

For the antibodies used in the above protocol A, emission spectra for the dyes are as follows: DAPI was imaged at 455 nm, anti-CD3 was imaged at 555 nm, and anti-Caspase 1 was imaged at 488 nm. FIG. 2 shows a representative image of intestinal epithelial cells stained (i.e., immunostained) for activated caspase 1. The T cells present in the slide are identified by co-staining with an antibody that specifically binds to CD3, a cell surface molecule associated with the T cell receptor in T cells. In FIG. 2, the white arrow points to a green-stained intestinal epithelial cell that stained positive for expression of caspase 1, and the white arrow head (i.e., triangle) points to a red-stained T cell (an intra-epithelial lymphocyte, or IEL) that stained positive for expression of both CD3 and caspase 1.

Protocol B: TUNEL Staining Protocol for Paraffin-Embedded Mucosal Biopsy Samples Using Commercially-Available Staining Kits.

TUNEL (Terminal deoxynucleotidyl transferase dUTP nick end labeling) staining is a method for detecting DNA fragmentation by labeling the terminal ends of nucleic acids. Since apoptosis causes fragmentation of DNA, the TUNEL assay is a common method for DNA fragmentation that results from apoptotic signaling cascades. The assay relies on the presence of nicks in the DNA which can be identified by terminal deoxynucleotidyl transferase or TdT, an enzyme that will catalyze the addition of dUTPs that are secondarily labeled with a marker.

Step I. Deparaffinization

Place the slides in a rack, and perform the following sequential washes in Coplin jars or other container:
1. Xylene: 2×5 minutes
2. 100% ethanol: 2×5 minutes
4. 95% ethanol: 3 minutes
5. 70% ethanol: 3 minutes
6. 50% ethanol: 3 minutes
7. Distilled H$_2$O: 2×3 minutes Keep the slides in the distilled water until ready to perform antigen retrieval. Do not allow the slides to dry from this point onwards. Drying out may cause non-specific antibody binding and therefore high background staining on the tissue.

Step II. Antigen Retrieval

1. Pre-heat a water bath and antigen retrieval solution (10 mM sodium citrate buffer) to 95° C. Sodium Citrate Buffer (10 mM sodium citrate, 0.05% Tween 20, pH 6.0) is made as follows:

Tri-sodium citrate (dihydrate) 2.94 g
Distilled water 1000 ml
Mix to dissolve. Adjust pH to 6.0 with 1N HCl.
Add 0.5 ml Tween 20, mix well, and store at 4° C.

2. Place slides in pre-heated antigen retrieval solution (enough to cover the slides by several a few centimeters). Avoid using glass containers as these may crack in the heat. A plastic Tupperware with a lid to prevent evaporation works well or empty tip boxes with lids also work. Add a weight on the cover to prevent the container from floating around.
3. Incubate the slides for 20 minutes at 95 C.
4. When 20 minutes have elapsed, remove the container and slides from the water bath. Allow the slides to cool at room temperate, still immersed in the antigen retrieval solution, before removing them from the container.

Step II. Nuclear Staining

At this point, follow the protocol provided by the commercially-available kit. Below is an abbreviated and adapted protocol for the Trevigen TACS® 2 TdT-Fluor In Situ Apoptosis Detection Kit, commercially available from Trevigen (Gaithersburg, Maryland) Cat #: 4812-30-K.

1. Immerse sample in 1×PBS for 10 minutes with gentle agitation.
2. Cover sample with 50 μl of Proteinase K Solution for 15 minutes. The Proteinase K Solution (per sample) contains as follows: 50 μl Apoptosis Grade™ Water and 1 μl Proteinase K
3. Wash the samples in deionized water for 2 minutes. Repeat with a second wash.
4. Immerse the samples in 1×TdT Labeling Buffer for 5 minutes. The TdT Labeling Buffer contains 45 ml Deionized Water and 5 ml 10×TdT Labeling Buffer (from the Trevigen kit).
5. Cover sample with 50 μl of Labeling Reaction Mix (from the Trevigen kit) and incubate for 60 minutes at 37° C. in a humidity chamber. The Labeling Reaction Mix per sample contains 1 μl TdT dNTP, 1 μl 50×Cation (Mg2+, Mn2+, or Co2+), 1 μl TdT Enzyme (Avoid repeated freeze-thaw), and 50 μl 1×TdT Labeling Buffer (from the Trevigen kit)
6. Immerse the samples in 1×TdT Stop Buffer for 5 minutes. The TdT Stop Buffer contains 45 ml Deionized Water and 5 ml 10×TdT Stop Buffer (from the Trevigen kit)
7. Wash the samples twice in 1×PBS, for 2 minutes each.
8. Cover sample with 50 μl of Strep-Fluor Solution and incubate for 20 minutes in the dark. The Strep-Fluor Solution contains 200 μl 1×PBST (1×PBS with 0.05% Tween 20) and 1 μl Strep-Fluorescein.
9. Wash the samples three times in 1×PBS, 2 minutes each.
10. Mount glass coverslip using 90% glycerol and view under fluorescence microscope using a 495 nm filter.

Figure 3A:
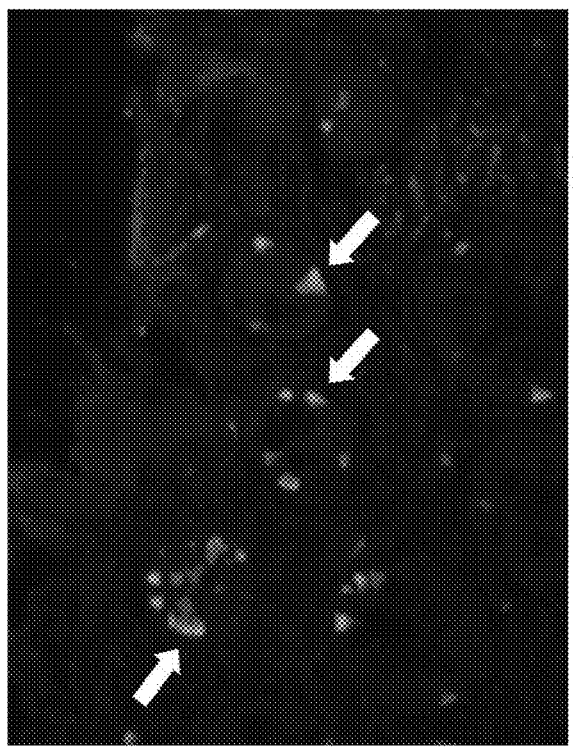
FIGS. 3A and 3B are photographic images showing the staining of intestinal epithelial cells (IECs) for nuclear fragmentation using a commercially available TUNEL stain (FIG. 3A) or for activated caspase 3 (FIG. 3B).
Figure 3B:
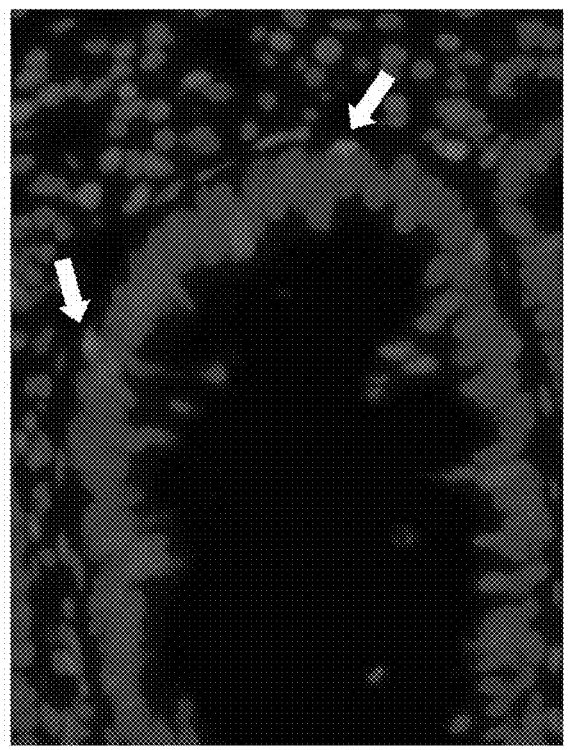

FIGS. 3A and 3B show representative images of intestinal epithelial cells stained (i.e., immunostained) for TUNEL (e.g., using Protocol B above) (FIG. 3A) and activated caspase 3 (e.g., using Protocol A above) (FIG. 3B). In FIG. 3A, the arrows points to intestinal epithelial cells staining positive for nuclear fragmentation using a commercial kit staining for TUNEL-positive cells. In FIG. 3B, the arrows point to intestinal epithelial cells staining positive for expression of caspase 3.

Example I

The major aim of this Example I is to improve patient selection for vedolizumab for the treatment of Crohn's disease and ulcerative colitis by assessing the functional status of the intestinal barrier prior to therapy. Biologic therapies such as anti-tumor necrosis factor (TNF), anti-IL12/23 agents, and anti-integrin agents have had a clinical response rate of about 50% for the past decade. Vedolizumab, a monoclonal antibody that specifically binds to integrin $\alpha_4\beta_7$ and sold under the name ENTYVIG® by Takeda Pharmaceuticals) was approved for clinical use in 2014 and has been widely used in patients who have failed to respond to other anti-TNF agents. However, its clinical response rate, particularly for Crohn's disease, was low compare to anti-TNF agents. This study has been designed to improve the therapeutic response to vedolizumab through better patient selection.

Studies over the past two decades have convincingly demonstrated that barrier disruption plays a significant and important role in the pathogenesis of mucosal inflammation in inflammatory bowel disease (IBD). Barrier disruption exposes the sub-epithelial immune system to resident microbes and induces the secretion of TNF-α and other pro-inflammatory cytokines, which in turn induces shedding of epithelial cells from the intestine and promotes further inflammation and increased barrier dysfunction.

This Example I is based on the discovery that assessment of the intestinal barrier function of biopsy samples can serve as an important prognostic tool for predicting the clinical response to vedolizumab in patients suffering from inflammatory bowel disease (e.g., Crohn's disease (CD) patients and ulcerative colitis patients). In some embodiments, the assessment of the intestinal barrier function of biopsy samples can serve as an important prognostic tool for predicting the clinical response to vedolizumab in patients likely to suffer in the future from irritable bowel syndrome and patients likely to suffer in the future from inflammatory bowel disease To do this, the clinical response to vedolizumab in Crohn's patients and ulcerative colitis patients who have been stratified by the mucosal barrier function status of pre-treatment biopsy samples from the terminal ileum is determined. A determination will be made as to whether the barrier status of the colon reflects that of the terminal ileum.

This Example I will allow improvement of patient selection, which will improve the therapeutic response to vedolizumab and enable clinicians to alter the course of disease and improve patient outcomes in a more cost-effective manner.

For this Example I, a study of pre-treatment mucosal biopsy samples collected from CD patients who are being treated or had previously been treated with vedolizumab (an anti-integrin agent) will be conducted. These biopsy samples will be analyzed for intestinal barrier function using previously reported techniques with appropriate modifications (unpublished). The clinical response of CD patients and ulcerative colitis patients to vedolizumab will be stratified by the baseline functional status of the mucosal barrier in each sample. The response rate is expected to be in the range of 70 to 80% in patients with gap density or positively stained activated caspases in the range of under 3 to 4% for vedolizumab for the treatment of both Crohn's disease and ulcerative colitis.

The primary objective of this Example I is to improve patient selection for vedolizumab therapy based on the pre-treatment functional status of the mucosal barrier, thereby improving clinical response to the therapy. The primary study end-point will be the determination of therapeutic responses to vedolizumab in Crohn's patients and ulcerative colitis patients stratified by pre-treatment barrier status. The secondary end-point will be the completion of a sensitivity analysis determining the cut-point for mucosal barrier dysfunction: this cut-point will yield the highest clinical response rate to vedolizumab in CD patients and ulcerative colitis patients for those who are below the value; while the lowest response rate for those who are above the value. The cut-point is the value that separates mild from severe barrier dysfunction. Since mucosal TNF activation does not occur in mild barrier dysfunction which is below the value, vedolizumab is the ideal therapy. In more severe barrier dysfunction, which is above the cut-point, mucosal TNF activation occurs and anti-TNF therapy is the more appropriate treatment. The mucosal barrier based therapeutic approach that will optimize response to anti-integrin and anti-TNF agents are shown in FIG. 1.

The secondary objective of this Example I is to determine whether barrier function status of the colon biopsies have similar predictive value for therapy as the terminal ileal samples. Assessment of mucosal barrier function with cell extrusion has been evaluated and validated in the terminal ileum of IBD patients and rodent model of disease (Liu J J, Davis E M, Wine E, Lou Y, Rudzinski J K, Alipour M, Boulanger P, Thiesen A L, Sergi C, Fedorak R N et al: Epithelial cell extrusion leads to breaches in the intestinal epithelium. Inflammatory bowel diseases 2013, 19(5):912-921; Liu J J, Rudzinski J K, Mah S J, Thiesen A L, Bao H, Wine E, Ogg S C, Boulanger P, Fedorak R N, Madsen K L: Epithelial gaps in a rodent model of inflammatory bowel disease: a quantitative validation study. Clinical and translational gastroenterology 2011, 2:e3, Kiesslich R, Duckworth C A, Moussata D, Gloeckner A, Lim L G, Goetz M, Pritchard D M, Galle P R, Neurath M F, Watson A J: Local barrier dysfunction identified by confocal laser endomicroscopy predicts relapse in inflammatory bowel disease. Gut 2012, 61:1146-1153). Loss of mucosal barrier function also occurs in the duodenum of both adult and pediatric Crohn's patients (see Lim L G, Neumann J, Hansen T, Goetz M, Hoffman A, Neurath M F, Galle P R, Chan Y H, Kiesslich R, Watson A J: Confocal endomicroscopy identifies loss of local barrier function in the duodenum of patients with Crohn's disease and ulcerative colitis. Inflammatory bowel diseases 2014, 20(5):892-900; and unpublished results). This finding suggests that innate immune-mediated epithelial cell deaths (pyroptosis) may occur throughout the gastrointestinal tract. CD is a disease that can affect tissues anywhere from the mouth to the anus. Thus, staining of oral/buccal mucosal biopsies or swabs for activated caspase staining may have similar predictive value for IBD therapy.

Although the exact trigger(s) for the innate immune activation in Crohn's disease have not been identified, the offending agent(s) are likely passing through the entire gastrointestinal tract. The innate immune activation resulting in mucosal barrier dysfunction observed in the terminal ileum is likely to occur in the colon as well. The objective of the second aim is to determine how closely the mucosal barrier function status in the colon reflects that of the terminal ileum. To reach that objective, regression analysis will be used to test the working hypothesis that markers of barrier function status measured in the colon can be used to predict with reasonable accuracy the same markers measured at the same time in the terminal ileum. In a cohort of 100 Crohn's patients, the barrier function of the conventional biopsy samples from the terminal ileum and the colon will be compared to evaluate the correlation of barrier function status in the two areas. Examination will then be made of how closely mucosal barrier function status in the colon reflects the barrier status in the terminal ileum.

To achieve the objective of improving patient selection and thus clinical response in CD patients, two study aims are set forth below:

Aim 1: To determine the clinical response to vedolizumab in Crohn's patients stratified by pre-treatment mucosal barrier function in the terminal ileum.

Aim 2: To determine whether the mucosal barrier function status of the colon reflects that of the terminal ileum.

Primary End-Points

Aim 1: Clinical response in CD patients is defined as a reduction of the Harvey-Bradshaw Index (HBI) by 5 points or more from pre-treatment baseline. Clinical remission is defined as an HBI of less than 5 (Harvey and Bradshaw, "A simple index of Crohn's-disease activity", *Lancet* 1980, 1(8167):514). For patients who do not have their HBI recorded, the assessment of their clinical status made during the most recent office visit will be used. The clinical responses and remission rates of Crohn's patients with mild and severe barrier dysfunction will be compared using Fisher's exact test.

Aim 2: Histologic evaluation of the conventional biopsy samples obtained from terminal ileum and the colon will be carried out. For barrier function assessment, activated caspase staining analysis will be performed. Standard methods will be employed, such as, for example, staining the biopsy samples by contacting the samples with, for example, fluorescently labeled antibodies that specifically bind to activated caspase 1 and caspase 3. Such antibodies are commercially available (e.g., from Cell Signaling Technology, Inc., Danvers, Massachusetts; from Abcam, Cambridge, Massachusetts; Santa Cruz Biotechnology, Santa Cruz, California). Mucosal biopsy samples from the terminal ileum and the colon will be stained and analyzed for activated caspases. For each sample, the total number of cells in the epithelial surface and the number of cells positively stained for activated caspase-1 or caspase-3 will be manually counted and recorded by a blinded expert pathologist. The total number of cells staining positive for activated caspase-1 and caspase-3 will be combined and expressed as percentage of the total number of epithelial cells counted over all the biopsy samples. For each patient, eight images of cross-sectional views of villi will be obtained from the four biopsy samples. A minimum of three villi with proper cross-sectional orientations will be selected from all the biopsy samples for manual counting. Activated caspase staining will be expressed as a continuous variable of positive cell per 1000 cells counted.

Secondary End-Points
  Aim 1: To perform a sensitivity analysis to determine the cut-point (threshold) for using barrier dysfunction as an indicator for treatment with vedolizumab in Crohn's patients.
Patients and Methods
Inclusion Criteria:
  1. Patient was diagnosed with Crohn's disease or ulcerative colitis based on standard clinical, radiological, endoscopic and histological criteria.
  2. Biopsies were obtained prior to the initiation of vedolizumab therapy, which had been prescribed because of moderate to severe flare, steroid dependence, failure of biologic therapies, or allergies or adverse reactions to other agents.
  3. Patient age is from 18 to 75 years.
Exclusion Criteria:
  1. Patient has had previous exposure to vedolizumab.
  2. Biopsies of the terminal ileum, colon and/or rectum were not obtained during the colonoscopy.
  3. Biopsies were obtained after vedolizumab therapy.
Study Procedure
  Patients on vedolizumab therapy will be screened using a clinical study information questionnaire. Relevant information will be collected and entered into the study database. Pre-treatment intestinal biopsy samples that fulfill the inclusion and exclusion criteria listed above will be retrieved from each study center for 100 CD patients who are currently or were previously on vedolizumab therapy. A detailed sample size calculation is provided in Statistical Methods section below. Mucosal biopsies from the terminal ileum and colon (proximal, distal colon, and the rectum) will be retrieved as either sectioned specimens or as paraffin blocks and sent to Central Arkansas Veterans Healthcare System (CAVHS) for analysis of barrier function status. For each patient, 2 to 4 biopsies from all locations listed above will be analyzed. For each patient, we will also conduct a retrospective review of the medical history and the endoscopic findings of the colonoscopies. The clinical responses to vedolizumab therapy and disease remission rates will be evaluated and stratified by barrier function status.

Study Duration
  Institutional Review Board (IRB) approval and chart review is anticipated to take 3 to 6 months for each study center. Biopsy samples will be sent for analysis at CAVHS over approximately a 12-month period. Data analysis will take 6 months to complete after all samples are analyzed. Thus, the total study duration will be about 24 months.
Study Enrollment and Timelines
  The five study sites with significant vedolizumab experience have already obtained the biopsy specimens for the proposed study from clinically indicated colonosocopies. After obtaining IRB approval-which should take no more than three months for a retrospective study that poses no additional risk to patients, specimens will be pulled from the pathology archives of each institution. Since the colonoscopies will likely have been done within the past three years, most institutions should have the biopsy samples stored on site. Even if some samples have been sent for storage and longer retrieval times are required, an average rate of 10 samples arriving each month are projected for a total duration of no more than a year before all study samples have been received and analyzed.
Statistical Methodology
Sample Size Calculation
  The sample size calculation was performed for Aim 1 and based on the assumption of a difference in clinical response rate of 50% between patients with severe and mild mucosal barrier dysfunction, i.e. 20% versus 70% response rate to vedolizumab therapy. These response rates are conservative estimates based on previous reports of 77% difference in response rate, i.e. 15% versus 92% in TNF antibody negative vs. positive patients (Atreya R et al., *Nat Med* 2014, 20(3):313-318). A total of 30 patients (15 per group) would be needed to achieve 80% statistical power with a type I error ($\alpha$) of 0.05. To obtain 30 patient samples of sufficient quality for analysis of barrier function, we estimate that we will need to obtain samples from approximately 100 patients. Many patients (estimated to be 30%) will not have had ileal biopsies. Among the remaining 70% that did have ileal biopsies, we anticipate that approximately half of the samples will not contain tissues suitable for barrier function analysis. The analysis for barrier function can only be performed on mucosal tissue with intact villous architecture, and clinicians often take biopsies only from diseased areas. Hence, only 30 to 35 of the 70 ileal samples are expected to be appropriate for barrier analysis. It is nonetheless anticipated that sufficient samples will be available in each group (i.e., 15 with mild and 15 with severe barrier dysfunction) to allow the statistical comparisons to be completed.
Statistical Analysis
  For the primary study end-point of Aim 1 are expressed as binary response variables (clinical response or remission). As noted above, Fisher's exact test will be the most appropriate method for the comparison of proportions between the two mucosal barrier function groups. For each aim, the estimated odds ratio and a 95% confidence interval will be used to describe the association between barrier function status and the study end-points.
  For secondary end-point of Aims 1, a receiver operating characteristic (ROC) curve will be constructed to describe the relationship between barrier function and clinical response. The overall ability of barrier function to discriminate between patients who do and do not achieve clinical response via the area under the ROC curve (AUROC) will be described. The values of barrier function which optimize discrimination based on the following two metrics: (a) total sensitivity+specificity; and (b) overall classification rate will be reported. For each threshold value, the proportion of patients above and below the threshold and the associated sensitivity, specificity, overall classification rate, and likelihood ratio statistics will be reported.

For Aim 2, markers of barrier function status will be activated caspase staining observed on mucosal biopsy samples. The markers will be measured in the colon and the terminal ileum. Data for each marker will be summarized by organ site as a mean, an SD, a median, quartiles, and a range. For each marker for each patient, we will display the relationship between the marker's values measured in the terminal ileum versus the colon as a scatterplot annotated with both a Pearson and a Spearmann correlation coefficient. Using the scatterplots as a guide, we will regress the marker's values measured in the terminal ileum on its values measured in the colon. Specifically, the data will be randomly divided 2:1 into a training set and a test set, use the training set to develop the regression model, and use the test set to determine how accurately the regression model predicts marker values in the terminal ileum. To develop the regression model, a traditional least-squares regression will be used as the primary tool. Quadratic or other nonlinear terms will be included if the scatterplot's shape warrants them. Back-up tools will include median regression and Poisson regression. Point estimates with standard errors for the regression model's intercept, slope, and any nonlinear terms that may have been included will be reported. To characterize how well the regression model predicts terminal-ileum marker values in the test set, a scatterplot will be used to plot the test set's observed values in conjunction with the regression model's predicted means, 90% confidence interval, and 90% prediction interval. The number of test-set data points that fall outside the 90% prediction interval will be noted. A root-mean-square prediction error (RMSPE) from the residuals between observed and predicted terminal-ileum marker values in the test set will be computed and reported on. The ratio of the RMSPE to the SD of terminal-ileum values in the entire data set (110 data points) will be used to judge the quality of prediction, with small ratios (<25%) implying good quality.

Future studies examining the cost-effectiveness of vedolizumab treatment based on the new therapeutic paradigm will be undertaken. Economic analysis of this personalized approach will be important in demonstrating cost savings to the payers. Prospective validation study of the results from this retrospective study is also needed to apply the barrier assessment technique to the general patient population.

It is expected that the results from this Example 1 will show that a majority of patients (i.e., 50% or more of the patients) whose biopsy samples show a moderate amount of dysfunction at the intestinal barrier will have a beneficial response to treatment with vedolizumab. By "moderate" is meant that the level of active caspase 1 and/or active caspase 3 in these patients is about 1.5% to less than about 4-5% (e.g., less than about 4%). In other words, about 1.5 cells to fewer than about 5 cells per 100 intestinal epithelial cells tested will be positive for staining for active caspase 1 and/or active caspase 3. In another example, "moderate" also means that the number of gaps in the intestinal barrier is between about 1.5 to 5 gaps per 100 epithelial cells. Note that in normal intestinal epithelial cells from healthy volunteers, there is less than 1% caspase 1 positive cells (i.e., fewer than one caspase 1 positive cell per 100 cells).

Figure 4:
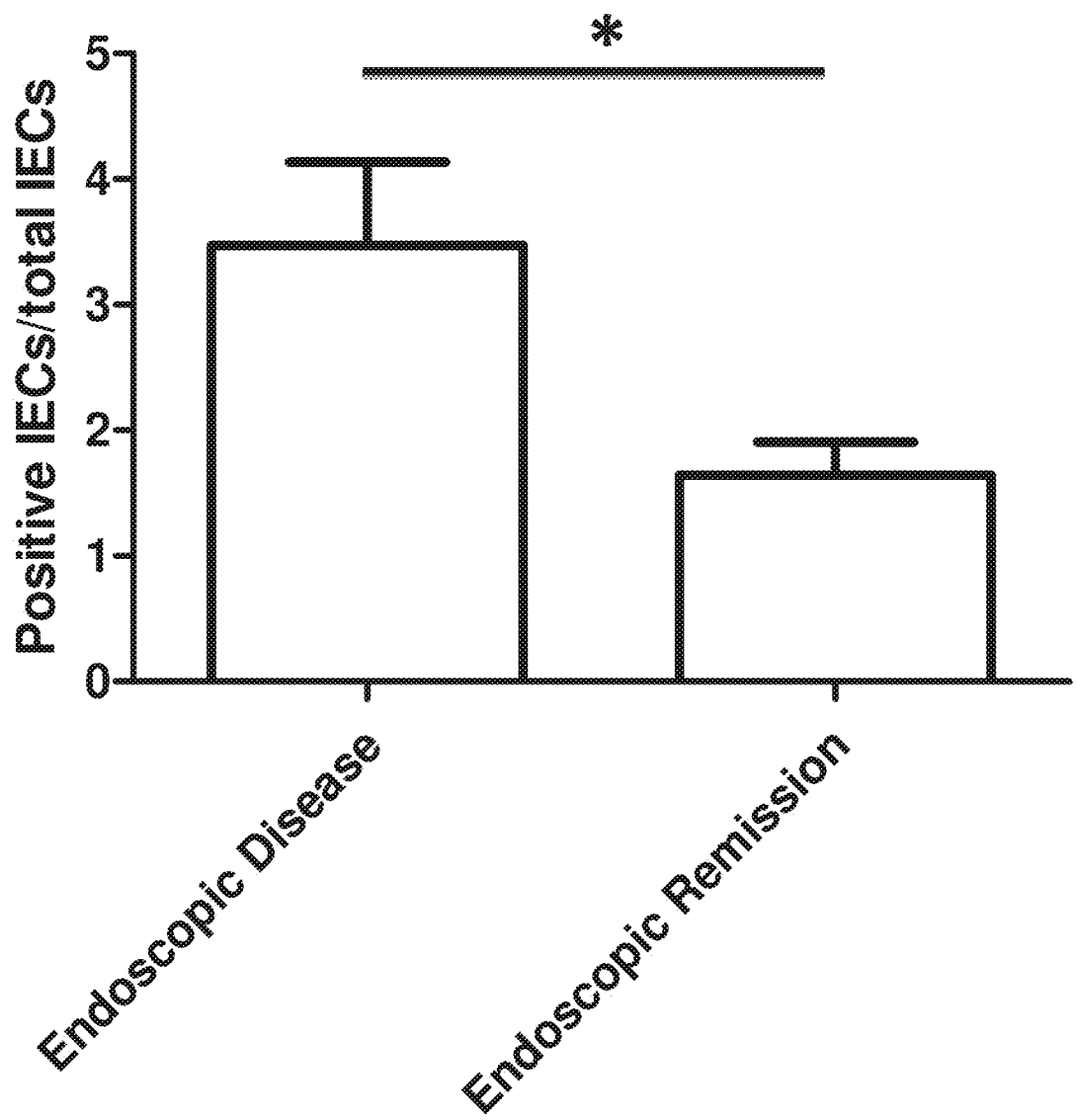
FIG. 4 is a bar graph showing the significant difference in the number of activated caspase 1 positive cells in IBD patients with disease (left column) or in IBD patients in remission (right column), as determined by endoscopy. The mean activated caspase-1 positive cells were: 1.5 in the endoscopic remission group, versus 3.5 in the diseased group (p=0.038).

Putting this example into practice, 27 patients with a median age of 59 years, with a median disease duration of 11 years (range 1 year to 36 years) were analyzed. Of these 27 patients, 11 patients had Crohn's disease and 16 patients had ulcerative colitis. Following treatment with aminosalacylates, steroids, immunomodulators or biologics, or combinations of any of the above therapies with a minimum duration of therapy of 3 weeks (range 3 weeks to 10 years). AS SHOWN IN FIG. 4, eight patients were in endoscopic remission and nineteen still had evidence of disease. Patients who responded favorably to biologic therapy, either single therapy or in combination with immunodulators and/or aminosalacylates were in endoscopic remission, and had lower activated caspase levels in their IECs than those patients who did not respond favorably to biologic therapy, or were just on aminosalacylates, or immunomodulators had evidence of endoscopic disease (see FIG. 4) The mean activated caspase-1 positive cells were: 1.5+/−0.75 in the endoscopic remission group, versus 3.5+/−2.5 in the diseased group respectively (p=0.038).

Note that in FIG. 4, the intestinal epithelial cells (IECs) stains were performed with immunohistochemistry (IHC) staining of intestinal biopsy samples taken from these patients using an anti-caspase 1 antibody.

Example 2

The major objective of this Example 2 is to develop an improved rate of response to biologic therapy for Crohn's disease (CD) based on the functional status of the mucosal barrier. The two aims of the study are to (1) evaluate the predictive value of barrier dysfunction for the therapeutic response to the anti-TNF agent certolizumab pegol or adalimumab in CD patients, and (2) determine the prognostic value of mucosal barrier dysfunction for disease relapse in CD patients on certolizumab pegol or on adalimumab.

In other words, the objective of this Example 2 is to determine the predictive value of mucosal barrier dysfunction for a therapeutic response to certolizumab pegol in CD patients. This objective is based on a hypothesis that barrier dysfunction is a potent predictor of response to anti-TNF therapy. This hypothesis is based on the following observations: (1) IBD patients with higher gap densities have higher mucosal pro-inflammatory cytokine levels (see Liu et al., "Epithelial cell extrusion leads to breaches in the intestinal epithelium", *Inflammatory Bowel Diseases* 2013, 19(5):912-921); (2) the highest rates of response to biologic therapy for Crohn's disease are seen in post-operative patients, with over 90% endoscopic remission rate at one year, and (3) prominent barrier dysfunction is observed at the anastomotic site in animal models of ileal resection (unpublished observations). The response rate is expected to be in the range of 70 to 80% for Crohn's patients with gap density or positively stained cells of over 6 to 7%.

A recent study of molecular imaging of the intestine with CLE in IBD patients has shown that anti-TNF therapy can result in a short-term clinical response rate of over 90% (Atreya et al., *Nat Med* 2014, 20(3):313-318). This result highlights the role of mucosal TNF levels in determining the response rate to biologic agents. IBD patients with higher gap densities have increased mucosal pro-inflammatory cytokine levels in their mucosal biopsy specimens (see Liu J J, et al., *Inflammatory bowel diseases* 2013, 19(5):912-921). Thus, CD patients with barrier dysfunction have increased mucosal TNF levels and are therefore more likely to respond (e.g., in a beneficial way) to certolizumab pegol or to or on adalimumab. Specifically, it may be possible to improve the long-term clinical response rate to certolizumab pegol from 50% in all CD patients to 80% to 90% in CD with barrier dysfunction.

Inclusion Criteria
1. Diagnosis of Crohn's disease based on standard clinical, radiological, endoscopic and histological criteria.
2. Patient about to be started on certolizumab pegol therapy or on adalimumab therapy because of moderate to severe flare, steroid dependence, failure of other therapies, or allergies or adverse reactions to other biologic agents.
3. Age 18 to 75 years.

Exclusion Criteria
1. Pregnancy/nursing.
2. Known allergies to fluorescein or shellfish.
3. Impaired renal function (serum creatinine over 1.5 mg/dL).
4. Uncontrolled or severe asthma.
5. Active infection.
6. Positive tuberculosis skin test.
7. History of systemic lupus.
8. Demyelinating neurological disease.
9. Congestive heart failure.
10. Prior or current treatment with anti-TNF agents.
11. Extensively resected small bowel.

The central hypothesis of this Example 2 is that mucosal barrier dysfunction is an important predictive tool for therapeutic response and disease relapse in CD patients.

Study Design

A prospective, blinded, observational study will be conducted of CD patients on or about to be initiated on certolizumab pegol therapy or on adalimumab therapy. Mucosal barrier dysfunction will be evaluated as a predictor for clinical response and relapse in patients on certolizumab pegol therapy or on adalimumab therapy.

Study Procedure

Each patient will undergo a colonoscopy with probe-based confocal laser endomicroscopy (pCLE) and mucosal biopsies. Blood and stool samples will be collected at baseline and at the one-year follow-up or at time of relapse. Detailed study methods are outlined below.

Biological measures in blood and fecal samples. All samples will be coded so that technicians will be blinded to the clinical status of each study patient. C-reactive protein levels in the blood will be measured using rate nephelometry. Blood serum samples will be collected at the time of colonoscopy or baseline clinic visit. Fecal calprotectin will be measured in luminal aspirate samples collected at the time of colonoscopy. Elevated fecal calprotectin indicates the migration of neutrophils to the intestinal mucosa, which occurs during intestinal inflammation, including inflammation caused by inflammatory bowel disease. All serum and fecal calprotectin samples will be stored at −80° C. until the time of assay.

Standard colonoscopy and biopsy data collection. High-definition white-light colonoscopy (without magnification or optical/digital enhancement technology) will be performed on all patients at baseline and at the one-year follow-up examination or at the first episode of disease flare. Endoscopic activity will be assessed using the simple endoscopic score for Crohn's disease (SES-CD). During these colonoscopies, four standard mucosal biopsy samples will be taken from the optical biopsies via pCLE will be performed: the terminal ileum and rectum. The tissue samples will be stored in liquid nitrogen while awaiting histopathologic and microbiome analysis.

Confocal laser endomicroscopy. Probe-based confocal laser endomicroscopy (pCLE) will be performed using previously reported methods (Hsiung et al., "Detection of colonic dysplasia in vivo using a targeted heptapeptide and confocal microendoscopy", Nature Medicine 2008, 14(4): 454-458; Liu J J, et al., "Increased epithelial gaps in the small intestines of patients with inflammatory bowel disease: density matters". Gastrointestinal Endoscopy 2011, 73(6):1174-1180). In brief, following intubation of the terminal ileum, 2.5 to 5 mL of 10% fluorescein will be administered intravenously to produce contrast in the image. An antispasmodic agent (glucagon or butylscopolamine) may also be given to reduce peristalsis and minimize movement artifacts in the images. Frame-by-frame confocal images of the terminal ileum (a survey of three sites for a total of 5 minutes) and of the rectum (a three-minute survey) will be collected using a previously described technique (Neumann et al., "Assessment of Crohn's disease activity by confocal laser endomicroscopy," Inflammatory Bowel Diseases 2012, 18(12):2261-2269). The total duration for recording of the pCLE images will be about 10 minutes per patient. Prior to study patient enrollment, each pCLE operator will undergo hands-on training to standardize the image acquisition techniques employed across all centers.

Post-hoc pCLE image analysis will be performed by two blinded expert reviewers using previously established criteria (Neumann et al., "Assessment of Crohn's disease activity by confocal laser endomicroscopy," Inflammatory Bowel Diseases 2012, 18(12):2261-2269). Epithelial gap density is a validated and reproducible measure of epithelial cell extrusion in the intestine, and it is also a surrogate marker for intestinal permeability. Each gap density measurement will be derived from the images of a minimum of three villi that have the highest number of epithelial gaps (normalized to the total number of epithelial cells in the villi) (Liu J J et al., "Mind the gaps: confocal endomicroscopy showed increased density of small bowel epithelial gaps in inflammatory bowel disease," Journal of Clinical Gastroenterology 2011, 45(3):240-245; Liu J J, et al., "Increased epithelial gaps in the small intestines of patients with inflammatory bowel disease: density matters". Gastrointestinal Endoscopy 2011, 73(6):1174-1180). Scoring of intestinal inflammation will be performed using previously established criteria for endomicroscopic assessment of inflammation in patients with Crohn's disease (see, e.g., Turcotte et al. "Increased epithelial gaps in the small intestine are predictive of hospitalization and surgery in patients with inflammatory bowel disease," Clinical and Translational Gastroenterology 2012, 3:e19]. These criteria include the number and tortuosity of colonic crypts, the appearance of the intestinal villi, the presence of microerosions, vascularity within the lamina propria, the number of goblet cells, the presence of cellular infiltrate within the lamina propria, and the density of the epithelial gaps.

Histological evaluation. Biopsies from the imaged mucosal areas will be fixed in formalin, embedded in paraffin, sectioned, stained with H&E, and analyzed by an expert pathologist who is blinded to the clinical status of each study patient. Histological scoring for the severity of acute inflammation will be based on the neutrophilic infiltration of the biopsied tissue. The histological score ranges from 0 (no acute inflammation) to 3 (massive acute inflammation), and was initially developed for ulcerative colitis (Riley et al., "Microscopic activity in ulcerative colitis: what does it mean?" Gut 1991, 32(2):174-178). In the absence of a validated histological scoring system for Crohn's disease, this scoring system was modified to quantify the degree of mucosal inflammation in the biopsied tissue. The modified score is composed of six indicators, each of which is rated on a scale of none (0) to severe (3 points). An experienced blinded pathologist will use this system to determine the degree of mucosal inflammation in each set of biopsies. The most severe changes within each set will be taken for grading. The six indicators are acute inflammatory cell infiltrate (neutrophils in the lamina propria), crypt abscesses, mucin depletion, altered surface epithelial integrity, chronic inflammatory cell infiltrate (mononuclear cells in the lamina propria), and crypt architectural irregularities. After morphologic evaluation by the pathologist, the histologic images will then be sent to a second pathologist for computerized image analysis to determine the predictive value of the images for disease relapse.

Microbiome analysis. DNA from one mucosal biopsy sample and from one luminal aspirate per patient will be extracted using a Qiagen Stool/Tissue kit and sent to an expert molecular microbiologist for analysis by 16S rRNA gene targeted sequencing using next-generation genetic sequencing instrumentation (HiSeq 2000, Illumina Inc., San Diego, CA). The 16S sequence reads will be analyzed using the "mothur" bioinformatics software package (http://www.mothur.org/) and classified using a Bayesian classifier from the Ribosomal Database Project from the Center for Microbial Ecology at Michigan State University (http://rdp.cme.msu.edu/classifier/classifier.jsp).

Clinical follow-up. Patients will be seen in clinic at baseline and every three months thereafter for one year in total (if the patient remains in remission) or for a shorter period if relapse occurs. Relapse is defined here as a Crohn's Disease Activity Index (CDAI) of more than 150 with an increase of at least 60 CDAI points from baseline. Patients will be instructed to communicate with the physician or research coordinator if they develop symptoms suggestive of an exacerbation, at which time a visit will be arranged to confirm the relapse. At each clinic visit and/or at the time of relapse, the CDAI will be calculated, blood will be drawn for measurement of C-reactive protein, stool samples will be taken for determination of fecal calprotectin level, and adherence with maintenance medication will be verified. Colonoscopies (with pCLE) will be arranged to assess the endoscopic severity of the disease in patients with relapse or at the end of one year.

Primary End-Points
Aim 1: To determine the clinical response rate at 3 months following induction therapy with certolizumab pegol or with Adalimumab. Clinical response is defined here as a decrease in CDAI of greater than 70. Clinical remission is defined as CDAI of less than 150. The clinical responses and remission rates of patients with normal and impaired barrier function (as shown by normal vs. elevated gap density) will be compared using Fisher's exact test.
Aim 2: To determine the relapse rate following induction therapy with certolizumab pegol in patients with mucosal barrier dysfunction and compare it to that of those without such dysfunction over one year of follow-up. Clinical relapse is defined here as a CDAI of greater than 150 with the increase of at least 60 points from baseline. The relapse rates of patients with normal and impaired barrier function will be compared using Fisher's exact test.

Secondary End-Points
Aim 1: To determine the clinical response rate and to acquire endoscopic evidence of mucosal improvement at one year after induction therapy with certolizumab pegol or with Adalimumab. Alterations in barrier function and microbial species induced by certolizumab pegol or with Adalimumab will be explored. The correlations between clinical response and endoscopic remission rate of patients with normal and impaired barrier function will be assessed.
Exploratory analysis of barrier dysfunction and microbiome analysis will be performed in collaboration with Dr. Brett Finlay of the University of British Columbia.
Aim 2: To correlate mucosal barrier dysfunction observed via pCLE (following induction therapy with certolizumab pegol or with Adalimumab) with (a) histologic evaluations of mucosal biopsy specimens, (b) the mucosal microbiome, and (c) biomarkers. In addition, features of the mucosal architecture seen using pCLE will be correlated with histologic findings.

Population and Number of Subjects

For Aim 1, CD patients with moderate to severe flare who are about to be placed on certolizumab pegol (N=30) or on Adalimumab (N=30) will be recruited. The sample size calculation was based on the assumption of a difference in clinical response rate of 55% between patients with normal and impaired mucosal barrier function (e.g., 25% versus 80% response rate). A total of 30 patients (15 per group) would be needed to achieve 80% statistical power with a type I error (a) of 0.05.

For Aim 2, CD patients who are on or initiating certolizumab pegol therapy (N=30) or on Adalimumab therapy (N=30) will be recruited. The sample size calculation was based on results obtained from our previous studies of disease relapse in IBD. To detect a difference in relapse rate of 50% between patients with normal and impaired mucosal barrier function (e.g., 5% versus 55% relapse at one-year follow-up), a total of 30 patients (15 per group) would be required to achieve 80% statistical power with a type I error (a) of 0.05.

CD patients undergoing routine colonoscopy prior to initiation of certolizumab treatment will have pCLE of the terminal ileum and rectum performed as in previous studies. Mucosal architecture and barrier function will also be examined by pCLE. The addition of pCLE to standard colonoscopy, although adding to the cost of the procedure, is expected to significantly improve the predictive value of colonoscopy for response to certolizumab in CD. Mucosal biopsies and luminal aspirates will be collected for histologic, cytokine, and microbial analyses. Biomarkers (C-reactive protein (CRP) and fecal calprotectin) will also be analyzed for comparison purposes.

Safety Variables

Adverse events related to the study procedure (confocal laser endomicroscopy) will be reported to the study site Institutional Review Board (IRB) and to the principal investigator. Since this study is designed to evaluate the predictive value of mucosal barrier dysfunction for response to clinically indicated certolizumab pegol therapy, a Data and Safety Monitoring Board will not be formed.

Duration

Patient enrollment is anticipated to take approximately 12 months, with a follow-up period of 12 months per study patient. Thus, the total study duration will be about 24 months. Data analysis will take another 3 months. The study is expected to be completed in 27 months.

Statistical Methodology
Sample Size Calculation

The study sample size of 30 patients for each Aim (15 with normal mucosal barrier function and 15 with barrier dysfunction) was determined to provide 80% statistical power to address both Aims 1 and 2. Because of the relatively small numbers of patients involved, Fisher's exact test will be used for the comparison of the groups' event rates. Through simulations, we estimate that having 15 patients in each group will provide approximately 78% power to detect a difference in clinical response rates of 55 percentage points (Aim 1) and 82% power to detect a difference in relapse rates of 5% vs 55% (Aim 2). (The secondary study end-points are exploratory and were not considered for the purposes of sample size estimation.)

Statistical Analysis

Both of the primary study end-points are expressed as binary response variables (clinical response at 3 months and disease relapse at one year). As noted above, Fisher's exact test will be the most appropriate method for the comparison of proportions between the two mucosal barrier function groups. For each Aim, the estimated odds ratio and a 95% confidence interval will be used to describe the association between barrier function status and the study end-points.

For secondary Aim 1, the concordance between the binary clinical response and endoscopic remission outcomes will be displayed via a 2×2 table. The agreement between the two outcomes will be quantified via odds ratio, percent agreement, and Cohen's kappa coefficient. These analyses will be carried out for the total cohort (N=30) as well as separately in each mucosal barrier function group (N=15 each). Differences in the strength of the relationships between the outcomes with respect to barrier function status will be assessed via a logistic regression model.

For secondary Aim 2, the histologic evaluation will result in scores ranging from 0 to 3 for each of six indicators, resulting in a total score ranging from 0 to 18. Each of these individual and total scores will be correlated with the gap density and the degree of inflammation determined by CLE (scored 0 to 3). For all comparisons, non-parametric methods (particularly Spearman's rank correlation and Somers' D, a measure of ordinal association) will be used be used to describe the concordance between parameters.

Example 3

The objective of this Example 3 is to determine the predictive value of mucosal barrier dysfunction for a therapeutic response to golimumab in UC patients. This objective is based on our hypothesis that barrier dysfunction is a potent predictor of response to anti-TNF therapy. This hypothesis is based on the following observations: (1) IBD patients with higher gap densities have higher mucosal pro-inflammatory cytokine levels (Liu J J, Davis E M, Wine E, Lou Y, Rudzinski J K, Alipour M, Boulanger P, Thiesen A L, Sergi C, Fedorak R N et al: Epithelial cell extrusion leads to breaches in the intestinal epithelium. Inflammatory bowel diseases 2013, 19(5):912-921); (2) the highest rates of response to biologic therapy for Crohn's disease are seen in post-operative patients, with over 90% endoscopic remission rate at one year (Regueiro M, Schraut W, Baidoo L, Kip K E, Sepulveda A R, Pesci M, Harrison J, Plevy S E: Infliximab prevents Crohn's disease recurrence after ileal resection. Gastroenterology 2009, 136(2):441-450 e441; quiz 716); and (3) prominent barrier dysfunction is observed at the anastomotic site in animal models of ileal resection (unpublished observations). Therefore, barrier dysfunction is expected to be a potent predictor of therapeutic response to golimumab in UC patients. The response rate is expected to be in the range of 70 to 80% for ulcerative colitis patients with gap density or positively stained cells of over 6 to 7%.

A recent study of molecular imaging of the intestine with CLE in IBD patients has shown that selecting patients who express mucosal TNF receptors can improve the short-term clinical response rate to over 90% (Atreya R, Neumann H, Neufert C, Waldner M J, Billmeier U, Zopf Y, Willma M, App C, Munster T, Kessler H et al: In vivo imaging using fluorescent antibodies to tumor necrosis factor predicts therapeutic response in Crohn's disease. Nat Med 2014, 20(3):313-318). This result highlights the role of mucosal TNF levels in determining the response rate to biologic agents. We have previously shown that IBD patients with higher gap densities have increased mucosal pro-inflammatory cytokine levels in their mucosal biopsy specimens (Liu J J, et al., "Epithelial cell extrusion leads to breaches in the intestinal epithelium," *Inflammatory bowel diseases* 2013, 19(5):912-921). Thus, it would be reasonable to assume that UC patients with barrier dysfunction have increased mucosal TNF levels and are therefore more likely to respond to golimumab. Specifically, it may be possible to improve the short-term and long-term clinical response rate to golimumab from 50% in all UC patients to 80% to 90% in selected UC patients, i.e. those patients with demonstrable barrier dysfunction. In view of the costs and complications associated with biologic therapy, an urgent and unmet need in the treatment of UC patients is the development of a prediction model that can identify patients who will respond favorably to golimumab.

The primary study end-point is clinical response/remission rate at three months and one year following induction therapy with golimumab. An analysis will be performed at 3 months following induction, i.e. 27 months after study initiation, with the final analysis to be performed at 36 months after study initiation. Clinical response is defined as a reduction of Mayo score by ≥30% and ≥3 points, with a rectal bleeding sub-score of ≤1 or a decrease in the bleeding sub-score of ≥1. Clinical remission is defined as a Mayo score of 2 points, without any sub-score>1.

The secondary end-points are endoscopic and histologic evidence of mucosal improvement at one year. Endoscopic mucosal improvement is defined as a Mayo endoscopy sub-score of 0 or 1. Patients will be followed for one year after initial colonoscopy with CLE.

Correlation of endomicroscopic findings with mucosal biopsies for histologic, microbiologic and cytokine profiles are performed in a secondary analysis.

Example 4

In this Example 4, biopsy samples containing intestinal epithelial cells were collected from patients suffering from inflammatory bowel disease. The biopsied cells were stained for activated caspase 1 expression using immunohistochemistry (IHC) as described above, and each patient categorized as a patient with high dysfunction (e.g., having activated caspase 1 of greater than about 4.5% (e.g., expression from about 5% to about 10% expression)) or a patient with moderate dysfunction (e.g., having activated caspase 1 of between about 1.5% to less than about 4.5%).

The patients were then randomly administered a therapeutically effective amount of either an anti-TNF agent or an anti-integrin agent.

Specifically, for these studies, twelve patients, with a median age of 44, and a median disease duration of 7.5 years (range of one year to eighteen years), were analyzed. Four patients had biopsy proven Crohn's disease, and the eight had biopsy-proven ulcerative colitis (UC). Six of the UC patients were treated with golimumab (a monoclonal antibody to TNF-alpha that is sold under the trademark Simponi® by Johnson & Johnson Corp.) One of the UC patients and one of the Crohn's disease patients were treated with infliximab, a chimeric monoclonal antibody that works against TNFα and is sold under the trademark Remicade by Johnson & Johnson Corp. The remaining three Crohn's disease patients and one UC patient were treated with vedolizamab, which is a monoclonal antibody that binds to integrin $\alpha_4\beta_7$ and is sold under the trademark Entyvio® by Millenium Pharmaceuticals, Inc.

Figure 5:
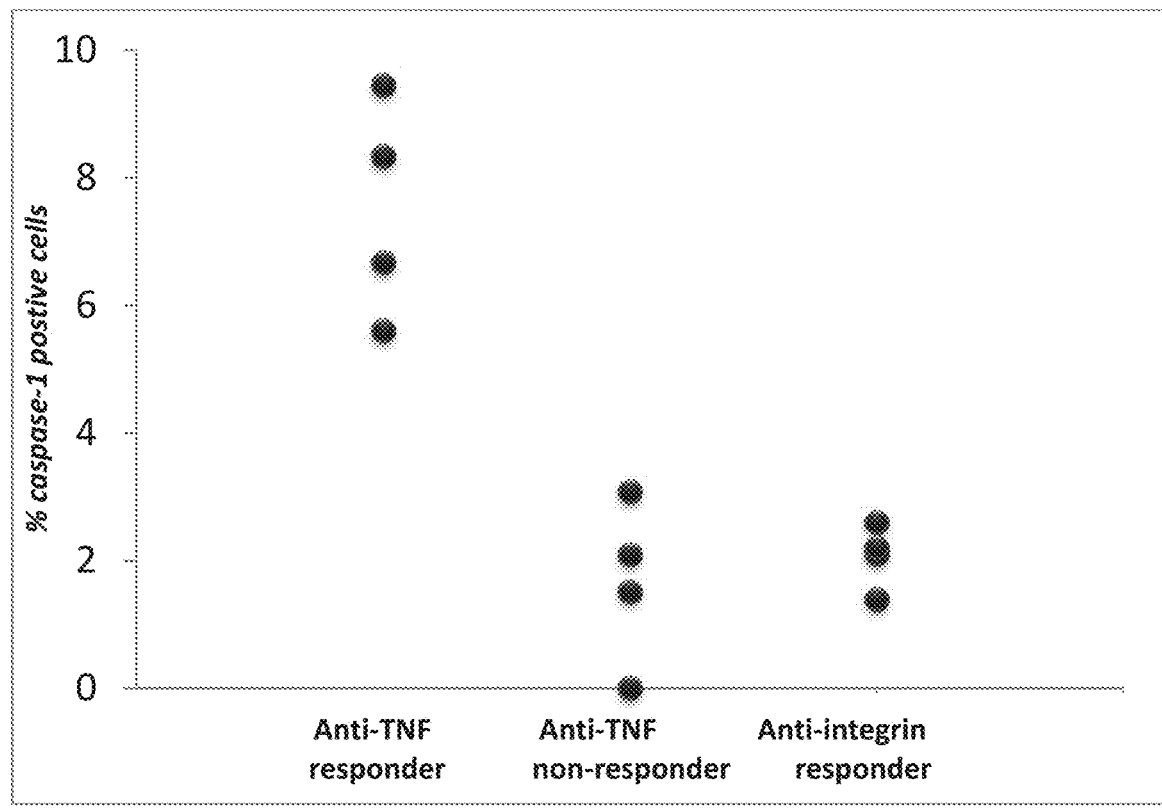
FIG. 5 is a dot plot showing the percentage of activated caspase 1 positive intestinal epithelial cells (IECs) cells taken from IBD patients who beneficially responded to anti-TNF therapy (left column, "Anti-TNF responder"), from IBD patients who did not beneficially respond to anti-TNF therapy (middle column, "Anti-TNF non-responder"), and from IBD patients who beneficially responded to anti-integrin therapy (right column, "Anti-integrin responder").

FIG. 5 shows the activated caspase levels of the patients before the start of therapy, and separates them into columns of patients who responded favorably to anti-TNF therapy ("Anti-TNF responder"), patients who did not responded favorably to anti-TNF therapy ("Anti-TNF non-responder"), and patients who responded favorably to anti-integrin therapy ("Anti-integrin responder")

As shown in FIG. 5, patients who had severe intestinal barrier dysfunction (between about 5% to about 10% activated caspase 1 positive cells) responded well to therapy with the anti-TNF agent. Patients who had moderate intestinal barrier dysfunction (between about 1% to 4% activated caspase 1 positive cells) did not have a beneficial response to the anti-TNF agent ("anti-TNF non-responder"). For patients with moderate intestinal barrier dysfunction who did not respond to the anti-TNF agent, some were subsequently treated with an anti-integrin agent (vedolizumab) and responded favorably (see "Anti-integrin responder" in FIG. 5).

With a minimum of 6 months clinical follow up (range 6 to 18 months) for the 12 patients on biologic therapy, 4 out of the 4 patients with severe barrier dysfunction on anti-TNF agents were in clinical remission; 4 patients with mild to moderate barrier dysfunction on anti-TNF agents had continued clinical symptoms of mild to moderate severity; the 4 patients on with mild to moderate barrier dysfunction on anti-integrin therapy, however, all achieved clinical remission. Here clinical remission for ulcerative colitis is defined as a partial Mayo score of less than 2 points, without any sub-score>1; for Crohn's disease, remission defined as a Harvey-Bradshaw Index (HBI) of less than 5.

All the patients whose data are shown in FIG. 5 were started on an anti-TNF agent (see left and middle columns in FIG. 5). For the patients who did not respond to anti-TNF therapy, colonoscopy was performed again while they were on the anti-TNF agent, and they still showed moderate barrier dysfunction. Those patients were treated with vedolizumab (the anti-integrin agent that binds to integrin $\alpha_4\beta_7$) and responded favorably (see far right column of FIG. 5).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of treating a patient afflicted with one or more symptoms of irritable bowel syndrome and inflammatory bowel disease comprising:
   (a) analyzing the status of an intestinal barrier in said patient; and
   (b) categorizing the patient's intestinal barrier status as severe dysfunction or mild/moderate dysfunction based on the amount of caspase-1 in said patient, and
   (c) treating said patient with a first agent if said patient has mild/moderate dysfunction or treating said patient with a second agent if said patient has severe dysfunction, wherein the status of the intestinal barrier is analyzed by measuring an amount of activated caspase-1 in buccal epithelial cells of the intestinal barrier;
   wherein an increase in the amount of activated caspase-1 in the range of two-fold to four-fold in buccal epithelial cells of an intestinal barrier of the patient as compared to a control amount of activated caspase-1, wherein the control is the amount of activated caspase-1 in buccal epithelial cells of an intestinal barrier of a healthy subject, indicates that the patient status is mild/moderate dysfunction;
   wherein an increase in the amount of activated caspase-1 in the range of four-fold to seven-fold in buccal epithelial cells of an intestinal barrier of the patient as compared to a control amount of activated caspase-1, wherein the control amount is the amount of activated caspase-1 in buccal epithelial cells of an intestinal barrier of a healthy subject, indicates that the patient status is severe dysfunction;
   wherein said first agent is selected from a group consisting of an anti-integrin agent, an anti-janus kinase agent, a sphingosine-1-phosphate receptor agonist agent, and a combination of two or more of an anti-integrin agent, an anti-janus kinase agent, and a sphingosine-1-phosphate receptor agonist agent; and
   wherein said second agent is selected from a group consisting of an anti-TNF-α agent, an anti-IL-12/23 agent, an anti-IL-12 agent, an anti IL-23 agent, and a combination of an anti-TNF-agent and an anti-IL-12/23 agent.

2. A method of treating a patient afflicted with one or more symptoms of irritable bowel syndrome and inflammatory bowel disease comprising:
   (a) analyzing the status of an intestinal barrier in said patient; and
   (b) categorizing the patient's intestinal barrier status as severe dysfunction or mild/moderate dysfunction based on the amount of caspase-1 in said patient, and
   (c) treating said patient with a first agent if said patient has mild/moderate dysfunction or treating said patient with a second agent if said patient has severe dysfunction;
   wherein status of the intestinal barrier is analyzed by counting a number of extrusion zones or gaps in histological staining of a buccal mucosal biopsy or a buccal mucosal swab of the intestinal barrier of said patient;
   wherein an increase in the number of extrusion zones or gaps in the range of two fold to four-fold in the buccal mucosal biopsy or the buccal mucosal swab of the intestinal barrier of the patient as compared to a number of extrusion zones or gaps in a buccal mucosal biopsy or a buccal mucosal swab of an intestinal barrier of a healthy subject, indicates that the patient status is mild/moderate dysfunction;
   wherein an increase in the number of extrusion zones or gaps in the range of four-fold to seven-fold in the buccal mucosal biopsy or the buccal mucosal swab of the intestinal barrier of the patient as compared to a number of extrusion zones or gaps in a buccal mucosal biopsy or a buccal mucosal swab of an intestinal barrier of a healthy subject, indicates that the patient status is severe dysfunction;
   wherein said first agent is selected from a group consisting of an anti-integrin agent, an anti-janus kinase agent, a sphingosine-1-phosphate receptor agonist agent, and a combination of two or more of an anti-integrin agent, an anti-janus kinase agent, and a sphingosine-1-phosphate receptor agonist agent, and wherein said second agent is selected from a group consisting of an anti-TNF-α agent, an anti-IL-12/23 agent, an anti-IL-12 agent, an anti IL-23 agent, and a combination of an anti-TNF agent, an anti-IL-12/23 agent.

3. The method of claim 2, wherein the status of the intestinal barrier is analyzed using confocal laser endomicroscopy or multi-photon confocal microscopy of the intestinal barrier.

4. The method of claim 1 or claim 2, wherein said first agent inhibits one or more of janus kinase, integrin and sphingosine-1-phosphate receptor.

5. The method of claim 1 or claim 2, wherein said second agent inhibits one or more of TNF-α, IL-12 and IL-23.

6. The method of claim 1 or claim 2, wherein the first agent is tofacitinib.

7. The method of claim 1 or claim 2, wherein the first agent is ozanimod.

8. The method of claim 1 or claim 2, wherein the first agent is selected from the group consisting of vedolizumab, natalizumab, and etrolizumab.

9. The method of claim 1 or claim 2, wherein the second agent is selected from the group consisting of adalimumab, infliximab, certolizumab pegol, golimumab, and etanercept.

10. The method of claim 1 or claim 2, wherein the second agent is ustekinumab.

11. The method of claim 1 or claim 2, wherein the inflammatory bowel disease is one or more of Crohn's disease, ulcerative colitis, indeterminate colitis and chemotherapy-induced colitis.

12. The method of claim 1 or claim 2, wherein said second agent is apremilast and prevents TNF-α production.

13. A method of improving the treatment of a patient with irritable bowel syndrome or inflammatory bowel disease comprising:
　(a) analyzing a status of an intestinal barrier in the patient to obtain a patient intestinal barrier status; and
　(b) categorizing the patient intestinal barrier status as severe dysfunction or mild/moderate dysfunction, and
　(c) wherein a patient categorized as having severe dysfunction is then treated with an agent that inhibits one or more of TNF-α, IL-12, and IL-23, or
　(d) wherein a patient categorized as having mild/moderate dysfunction is then treated with an agent that inhibits one or more of integrin, janus kinase, sphingosine-1-phosphate receptor, or a combination of two or more of integrin, janus kinase, and sphingosine-1-phosphate receptor;
wherein an increase in the amount of activated caspase-1 in the range of two-fold to four-fold in buccal epithelial cells of an intestinal barrier of the patient as compared to a control amount of activated caspase-1, wherein the control amount is the amount of activated caspase-1 in buccal epithelial cells of an intestinal barrier of a healthy subject, indicates that the patient status is mild/moderate dysfunction; and
　wherein an increase in the amount of activated caspase in the range of four-fold to seven-fold in buccal epithelial cells of an intestinal barrier of the patient as compared to a control amount of activated caspase-1, wherein the control amount is the amount of activated caspase-1 in buccal epithelial cells of an intestinal barrier of a healthy subject, indicates that the patient status is severe dysfunction.

14. A method of treating a patient afflicted with one or more symptoms of chronic gastrointestinal functional disorders comprising:
　(a) analyzing the status of an intestinal barrier in said patient; and
　(b) categorizing the patient's intestinal barrier status as severe dysfunction or mild/moderate dysfunction based on amount of caspase-1, and
　(c) treating said patient having mild/moderate dysfunction with an agent that inhibits one or more of integrin, janus kinase, sphingosine-1-phosphate receptor, or a combination of two or more of integrin, janus kinase, and sphingosine-1-phosphate receptor or treating said patient having severe dysfunction with an agent that inhibits one or more of TNF-α, IL-12, and IL-23;
wherein an increase in the amount of activated caspase-1 in the range of two-fold to four-fold in buccal epithelial cells of an intestinal barrier of the patient as compared to a control amount of activated caspase-1, wherein the control amount is the amount of activated caspase-1 in buccal epithelial cells of an intestinal barrier of a healthy subject, indicates that the patient status is mild/moderate dysfunction;
　wherein an increase in the amount of activated caspase-1 in the range of four-fold to seven-fold in buccal epithelial cells of an intestinal barrier of the patient as compared to a control amount of activated caspase-1, wherein the control amount is the amount of activated caspase-1 in buccal epithelial cells of an intestinal barrier of a healthy subject, indicates that the patient status is severe dysfunction.

15. The method of claim 14, wherein said first agent inhibits one or more of janus kinase, integrin and sphingosine-phosphate receptor, and wherein said second agent inhibits one or more of TNF-α, IL-12 and IL-23.

* * * * *